US008751248B2

(12) United States Patent
Muraca

(10) Patent No.: US 8,751,248 B2
(45) Date of Patent: Jun. 10, 2014

(54) METHOD, APPARATUS, AND MEDIUM USING A MASTER CONTROL FILE FOR COMPUTER SOFTWARE INTEROPERABILITY BETWEEN DISPARATE OPERATING SYSTEMS

(75) Inventor: John Muraca, Utica, NY (US)

(73) Assignee: Visual Telecommunications Network, Inc., McLean, VA (US)

( * ) Notice: Subject to any disclaimer, the term of this patent is extended or adjusted under 35 U.S.C. 154(b) by 985 days.

(21) Appl. No.: 09/853,703

(22) Filed: May 14, 2001

(65) Prior Publication Data

US 2002/0055917 A1 May 9, 2002

Related U.S. Application Data

(60) Provisional application No. 60/236,726, filed on Oct. 2, 2000, provisional application No. 60/221,558, filed on Jul. 28, 2000.

(51) Int. Cl.
*G06Q 50/00* (2012.01)
*G06Q 10/00* (2012.01)

(52) U.S. Cl.
USPC ............................... 705/2; 705/3

(58) Field of Classification Search
USPC ............................................... 705/2–3
See application file for complete search history.

(56) References Cited

U.S. PATENT DOCUMENTS

| | | | | |
|---|---|---|---|---|
| 5,325,294 A | * | 6/1994 | Keene | 705/3 |
| 5,499,293 A | * | 3/1996 | Behram et al. | 705/76 |
| 5,579,393 A | * | 11/1996 | Conner et al. | 713/176 |
| 5,664,109 A | * | 9/1997 | Johnson et al. | 705/2 |
| 5,737,539 A | * | 4/1998 | Edelson et al. | 705/3 |
| 5,903,889 A | * | 5/1999 | de la Huerga et al. | 1/1 |
| 5,918,229 A | | 6/1999 | Davis et al. | 707/10 |
| 5,924,074 A | * | 7/1999 | Evans | 705/3 |
| 5,937,421 A | | 8/1999 | Petrov et al. | 715/526 |
| 6,018,713 A | * | 1/2000 | Coli et al. | 705/2 |
| 6,023,510 A | * | 2/2000 | Epstein | 705/74 |
| 6,064,968 A | * | 5/2000 | Schanz | 705/1 |
| 6,073,136 A | | 6/2000 | Bertram et al. | 707/104.1 |
| 6,088,695 A | | 7/2000 | Kara | 707/10 |
| 6,102,855 A | | 8/2000 | Kehr | 600/300 |
| 6,112,183 A | * | 8/2000 | Swanson et al. | 705/2 |
| 6,256,627 B1 | | 7/2001 | Beattie et al. | 707/6 |
| 6,665,647 B1 | * | 12/2003 | Haudenschild | 705/2 |
| 6,785,810 B1 | * | 8/2004 | Lirov et al. | 713/165 |
| 6,988,075 B1 | * | 1/2006 | Hacker | 705/3 |
| 2001/0041991 A1 | | 11/2001 | Segal | 705/3 |
| 2003/0188200 A1 | | 10/2003 | Paquin | 713/202 |

OTHER PUBLICATIONS

De Moor, Towards a meta-syntax for medical edi, Jan. 1994, International Journal of Bio-Medical Computing, vol. 34 No. 1/4, p. 319-330.*

(Continued)

*Primary Examiner* — Tran Nguyen
(74) *Attorney, Agent, or Firm* — Staas & Halsey LLP

(57) ABSTRACT

A master control file enables application software to be ported between disparate operating systems of a computer without being updated by interfacing to portability enabling software, which interfaces with the disparate operating systems. Moreover, the application software includes medical software ported to a pocket device using the portability enabling software and the master control file.

36 Claims, 41 Drawing Sheets

(56) References Cited

OTHER PUBLICATIONS

Amit, Federated Database Systems for Managing Distributed, Heterogeneous, and Autonomous Databases, ACM Computing Surveys, vol. 22, No. 3, Sep. 1990.*
"TecKnowledge Healthcare Systems Inc. and ViTelNet Announce New Telehealth Alliance—Providing a Holistic Approach to Telehealth," http://www.vitelnet.com/profile_news/news_info.htm, dated Sep. 1, 1999, 2 pages.
ViTel Net Visual Telecommunications Network, Inc. brochure, "The Source for Telemedicine Solutions," 7 pages, including pages entitled "Leadership in multimedia information management and delivery systems," "About Us," "MedVizer Executive"/"MedVizer Interface Engine," "MedVizer Technology Approach," "MedVizer Store & Forward"/"MedVizer Web Environment," "MedVizer Video Conferencing (VTC)"/"MedVizer Acquisition", Visual Telecommunications Network, Inc.
ViTel Net, Inc. Press Release, May 3, 2000, "ViTel Net's Dvision Toolbox PACS, the Backbone of the Company's Telemedicine Solutions, Receives FDA Clearance," 1 page, Visual Telecommunications Network, Inc.
ViTel Net, Inc., Press Release, Jul. 20, 2000, ‹ ViTel Net's MedVizer TeleUltrasound Goes 'Live' in Northern Alberta Linking Rural Patients with Edmonton Radiologists, 2 pages, Visual Telecommunications, Inc.
ViTel Net, Inc., Press Release, Jul. 11, 2000, ‹ ViTel Net Awarded Costa Rica Telemedicine Network Project, 2 pages, Visual Telecommunications, Inc.
ViTel Net, Inc., Press Release, May 15, 2000, ‹ New, Windows Ce-based, Hand-held Telemedicine Data Collection Units for Home Care, Now Available from ViTel Net, 2 pages, Visual Telecommunications, Inc.
ViTel Net, Inc., Press Release, May 15, 2000, ‹ New, Portable MedVizer Post-Acute Care Solutions, Now Available from ViTel Net, 2 pages, Visual Telecommunications, Inc.
ViTel Net, Inc., brochure inserts (8 pages, Copyright 2000 Visual Telecommunications Network, Inc.), including pages entitled "MedVizer Executive (Patient Information Manager Desktop)", "MedVizer HomeCare Personal Assistant", "MedVizer Personal Physician Assistant", "MedVizer Post-Acute Care Solution", "MedVizer TeleRadiology and PACS Solution", "MedVizer TeleEchocardiogram Solution", "MedVizer TeleUltrasound Solution", "MedVizer Web Browser Enhancement Tools".
International Search Report issued Oct. 10, 2001 in corresponding PCT Application No. PCT/US01/23621 (1 page).
Written Opinion issued Jul. 25, 2002 in corresponding PCT Application No. PCT/US01/23621 (4 pages).
European Search Report issued Mar. 30, 2004 in corresponding European Application No. 01995252.6 (3 pages).
Office Action dated Jun. 9, 2004 in corresponding European Patent Application No. 01959252.6 (7 pages).
Office Action dated Dec. 2, 2004 in corresponding European Patent Application No. 01959252.6 (3 pages).
European Search Report dated Mar. 30, 2004 in corresponding European Patent Application No. 01959252.6 (3 pages).
ViTel Net brochure, 1998 (9 pages).
ViTel Net brochure, (13 pages) including: Children's National Medical Center Obtains Positive Results Using ViTel Net's MedVizer Tele-Echocardiography Solution, Press Release, Jun. 4, 2001 (1 page) ViTel Net Awarded Tele-Echocardiography Network Contract From St. Christopher's, Press Release, May 29, 2001 (1 page) ViTel Net Chose by the State of South Carolina's Hollings Cancer Center, Press Release, Jun. 1, 2001 (1 page) MedVizer Tele-Echocardiography brochure, Jun. 3, 2001 (10 pages).
POP3, SearchWebServices.com, (last updated on Feb. 22, 2004), printed on Apr. 28, 2005, 2 pages, http://searchwebservices.techtarget.com/sDefintion/0,,sid26_gci21805,00.html.
PFC 1939 (RFC 1939), RFC 1939—Post Office Protocol—Version 3, (dated May 1996), printed Apr. 28, 2005, 19 pages, http://www.faqs.org/rfcs1939.html.
PCT International Preliminary Examination Report, mailed Jan. 10, 2003 and issued in corresponding International Patent Application No. PCT/US01/23621.

* cited by examiner

Master Control File (MCF) – FIGURE 9

Server Side – Master Control File (Thin Client) – Figure 11A

DEFAULT.ASP                                    260

```
set DvMcf1=server.CreateObject("uDvMcf.DvMcf")
  DvMcf1.McfName = "c:\Vitelnet\Vitelnet.mcf"
      '// Submit for the set of records in the db
  RecordCount = DvMcf1.Submit(ln & Chr(0) & mm & Chr(0) & ssm & Chr(0))
  If DvMcf1.RecordCollection.Count = 0 Then
     '//get the first set of records in db
     RecordCount = DvMcf1.Submit("" & Chr(0) & "" & Chr(0) & "" & Chr(0))
  End If
  RecordsList.Clear
  RecordsList.AddItem "Select from this list."
```

Client Side – Master Control File (Thin Client) – Figure 11B

PAGE1.ASP                                    262

```
Sub ViewOcx1_ScrollChange
Dim TmpStr,Ptr if Tab <> "" then
   TabList.selectedindex = thisForm.ViewOcx1.ScrollIndex
   TmpStr = TabList.getValue(selectedIndex)
Else
   thisForm.ImageList.selectedindex = thisForm.ViewOcx1.ScrollIndex
   TmpStr = thisForm.ImageList.value
end if
  TmpStr = ImageList.getValue(thisForm.ViewOcx1.ScrollIndex)
  Ptr = instr (1,TmpStr,";")
  If Ptr = 0 then
     exit sub
  else
     thisForm.ViewOcx1.ShowImage = trim(mid(TmpStr,Ptr+1,Len(TmpStr)))
  end if
End Sub
```

FIGURE 12

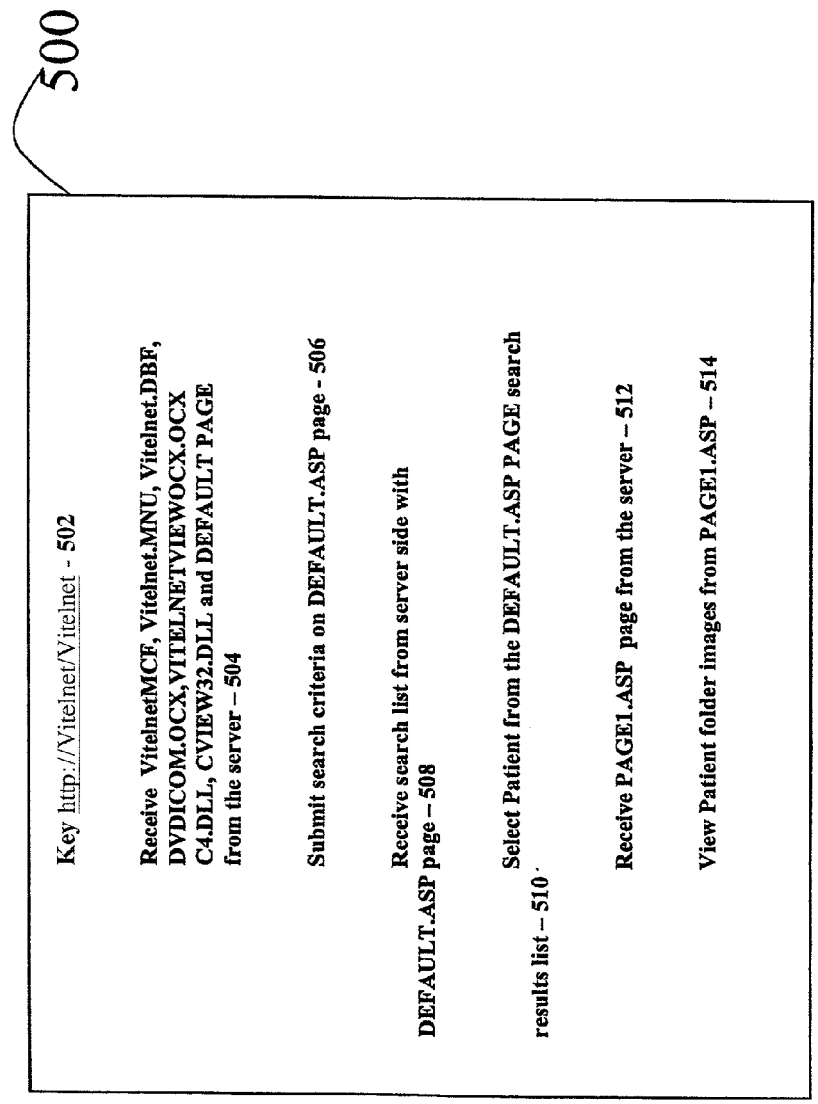

Key http://Vitelnet/Vitelnet - 502

Receive VitelnetMCF, Vitelnet.MNU, Vitelnet.DBF, DVDICOM.OCX,VITELNETVIEWOCX.OCX C4.DLL, CVIEW32.DLL and DEFAULT PAGE from the server – 504

Submit search criteria on DEFAULT.ASP page - 506

Receive search list from server side with DEFAULT.ASP page – 508

Select Patient from the DEFAULT.ASP PAGE search results list – 510

Receive PAGE1.ASP page from the server – 512

View Patient folder images from PAGE1.ASP – 514

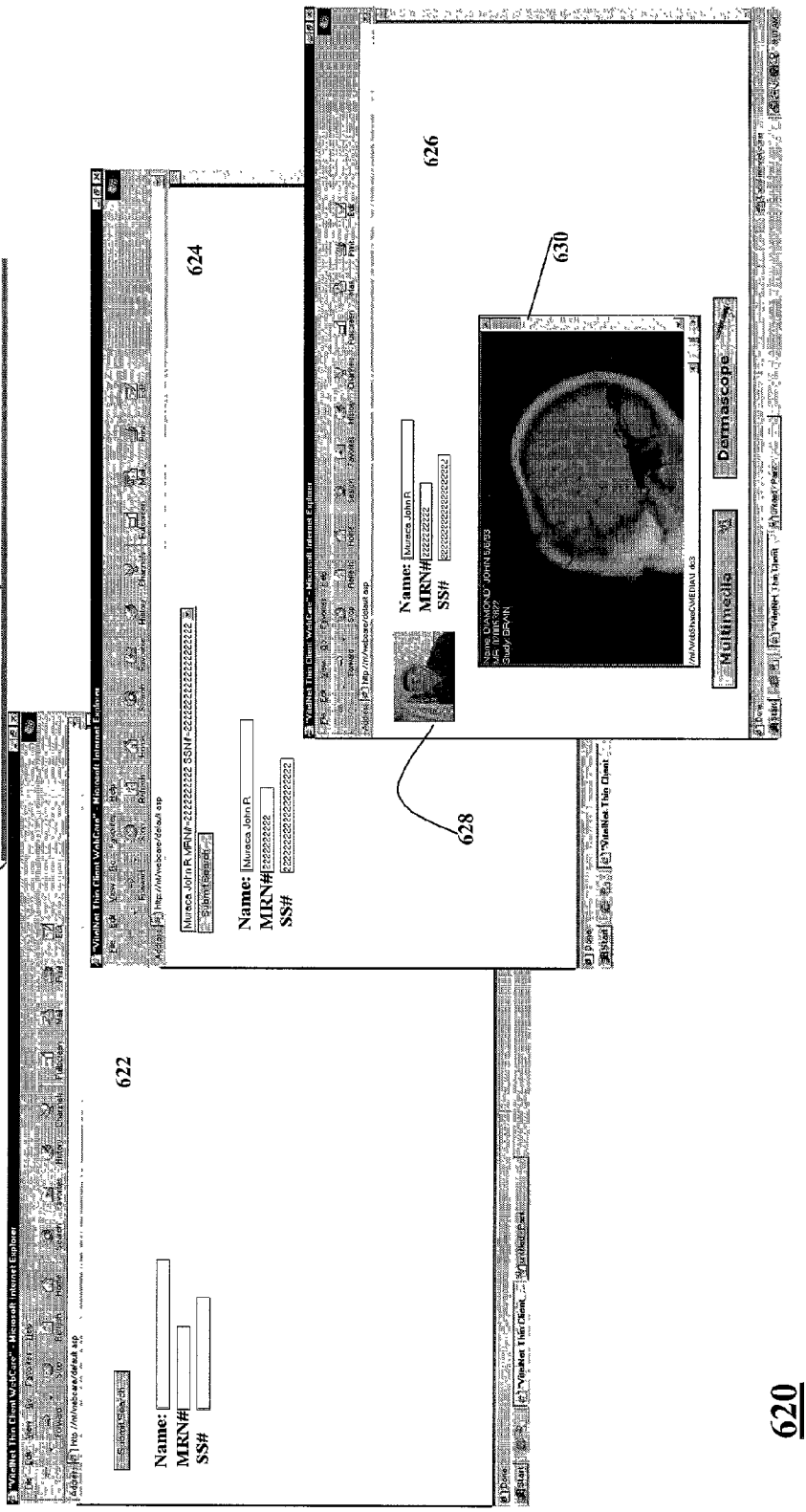

FIGURE 14

Master Control File (Database Pointer)

Master Control File (Multiple Forms)

Pointer to and Name of Graphic Image(s) - This is the image(s) that displays when the MedVizer application is executed.

Master Control File (Field Locations & Attributes) – FIGURE 17

Database Field Location - This is the top X Y coordinates that define the location that the database field will be displayed on the Graphic image when the MedVizer application is executed.

Database field attributes (Field Length, Alpha/Num, Numeric Only)
    Date (North American/European Format)
        Auto filled with system date when database record is created.
        Auto fill when database record is modified.
        Fill from keyboard.
    Image List – Stores list of archived documents maintained and displayed from this field
    MCF Link – Points to another MCF
    Invisible - Field data is not displayed
    Constant -Data is auto entered with a constant
    Skip – Prevents from anchoring cursor on field.
    Required - Data must be entered into this field
    Lock – Prevents user from entering/changing field content.
    Font - Defines font selection for this field
    Tab Order – Sets the tabbing order when Tab key is pressed.

MedVizer Object Storage/Retrieval (Image List Field)

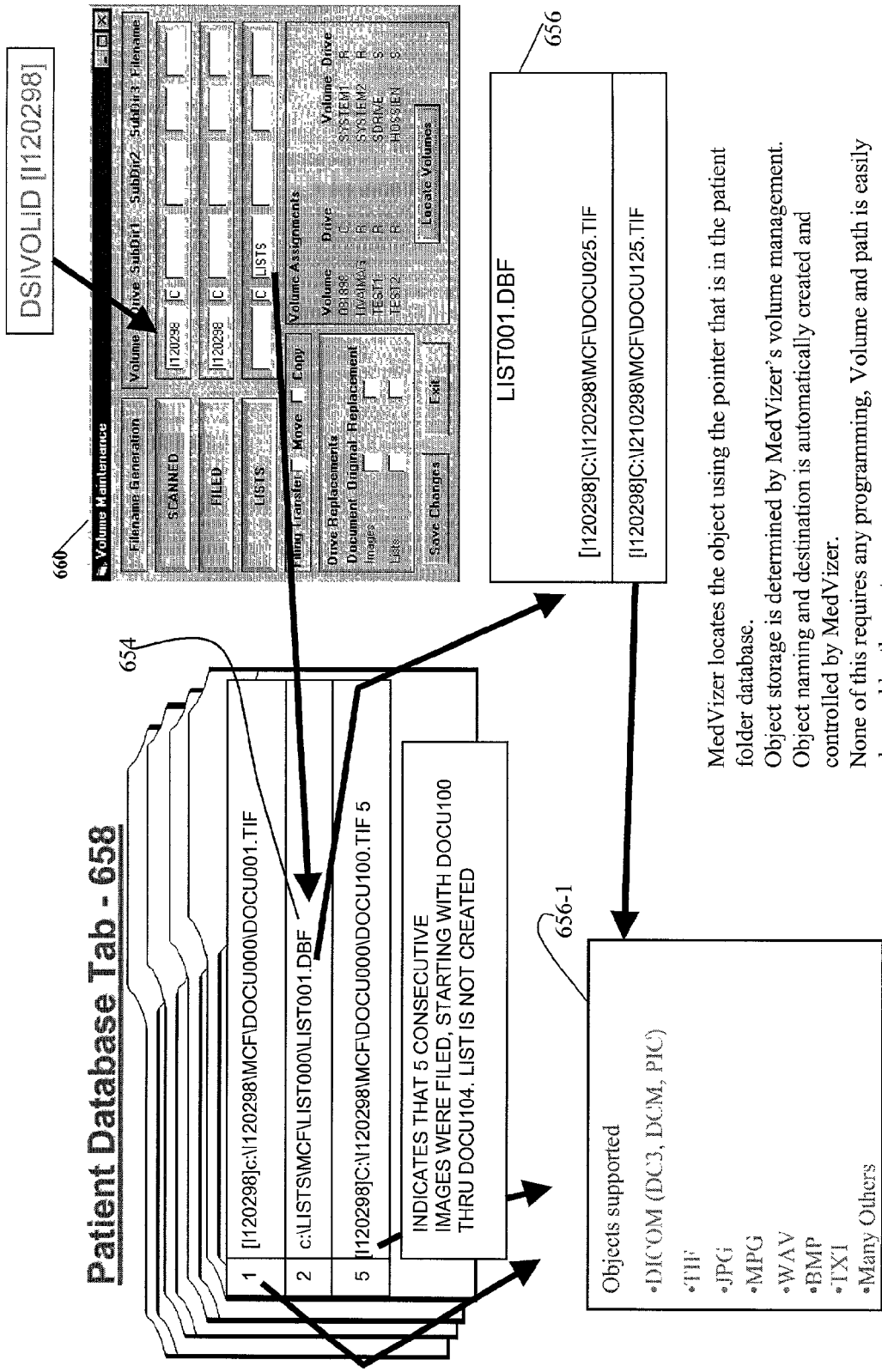

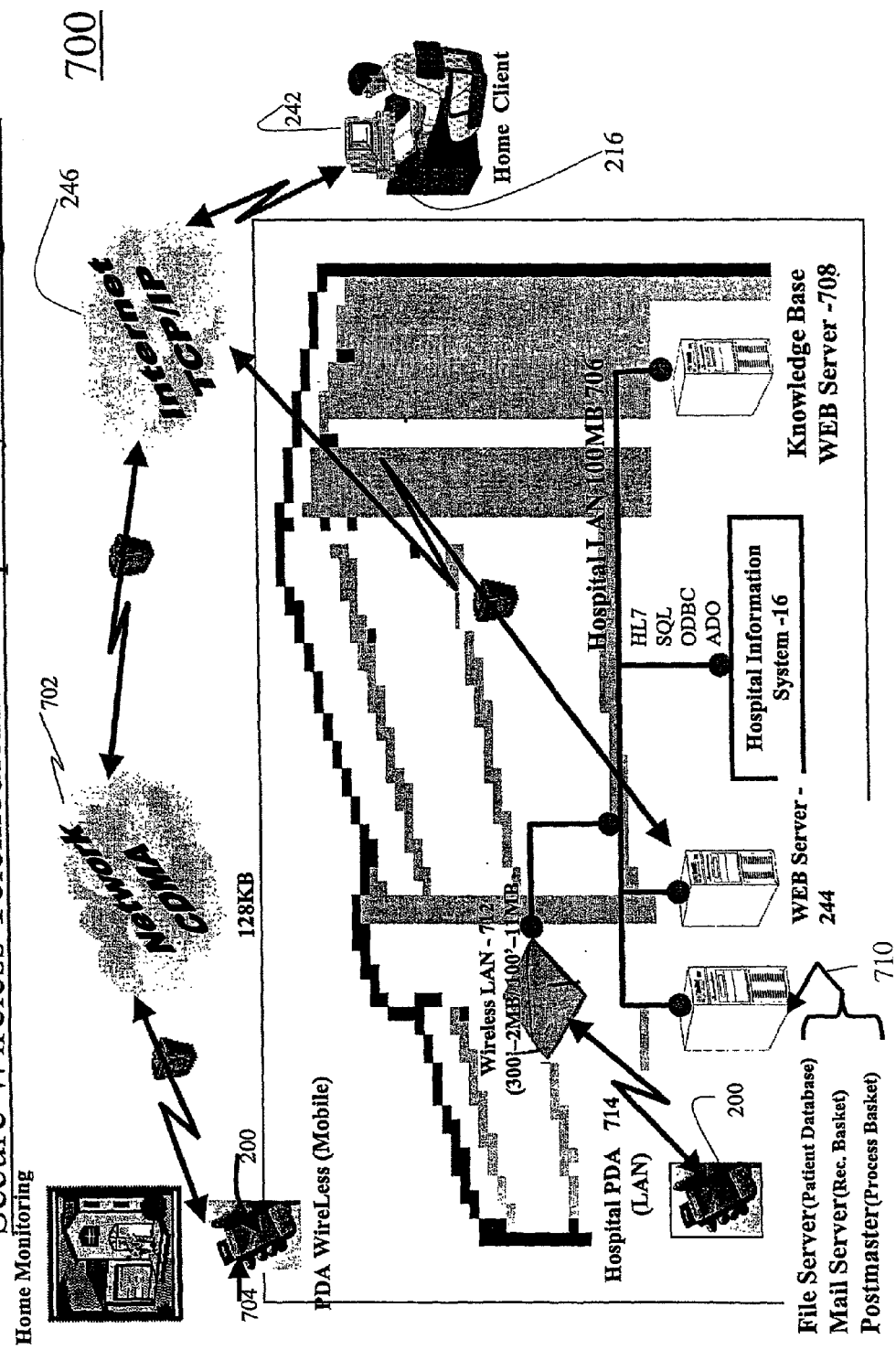

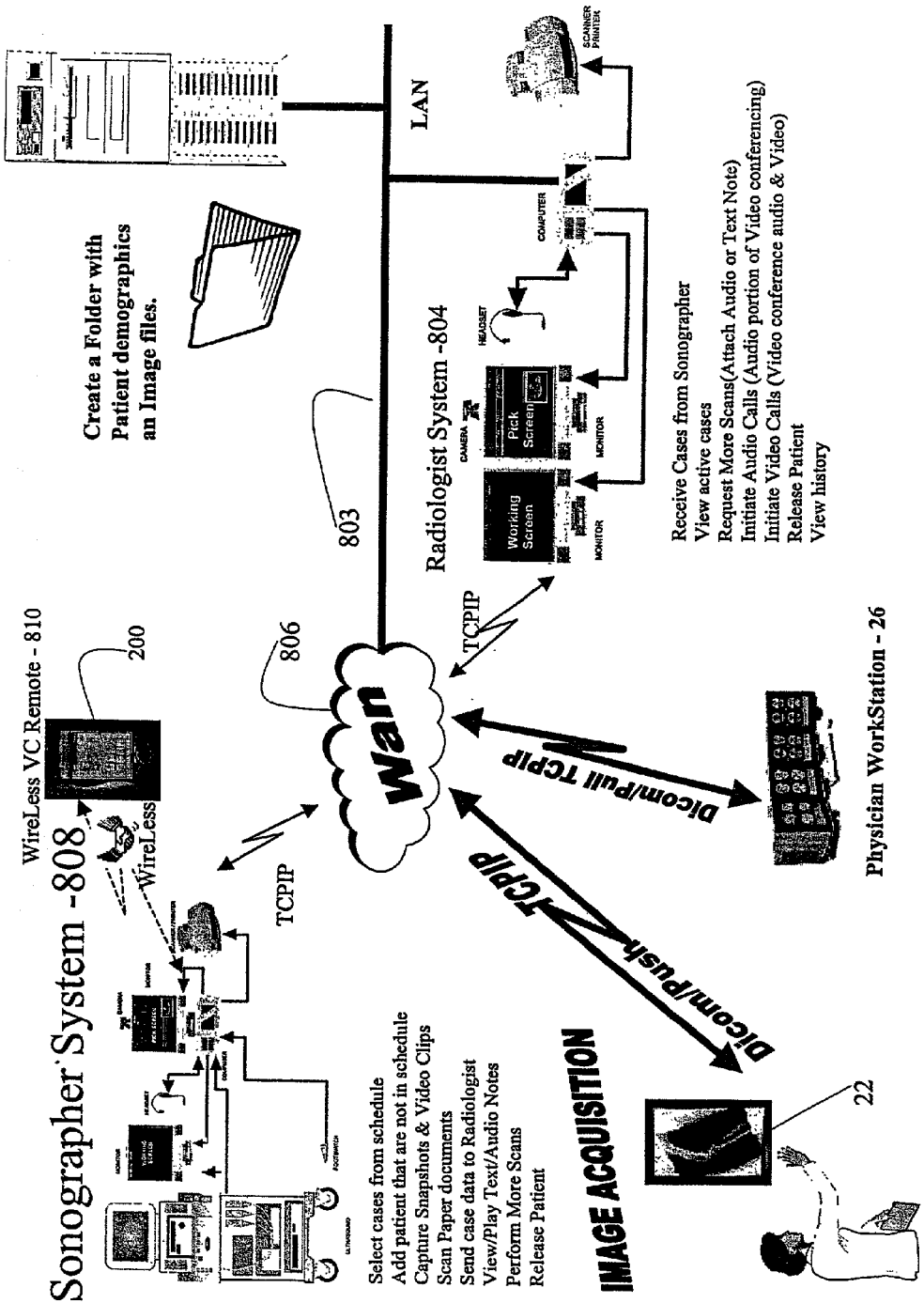

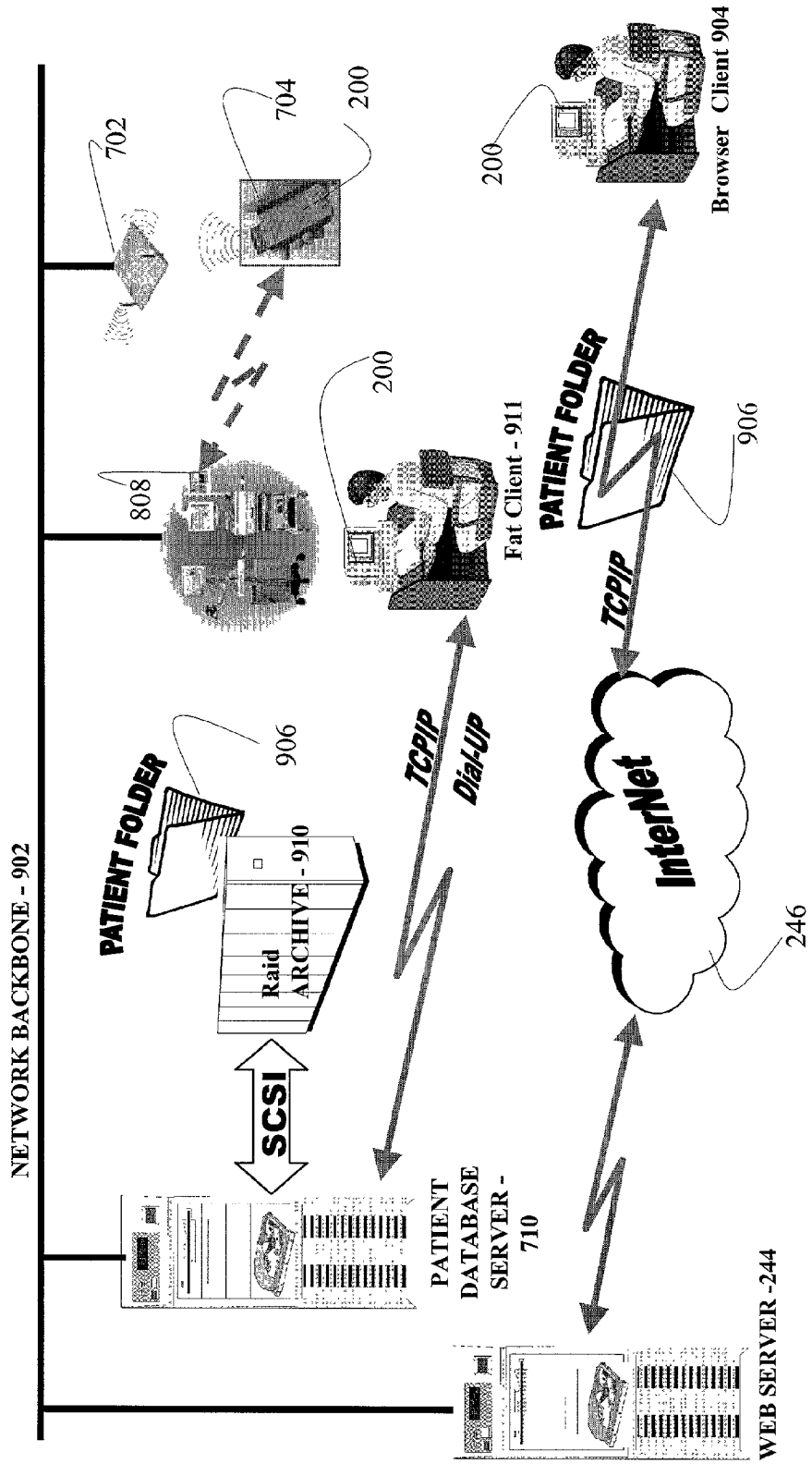

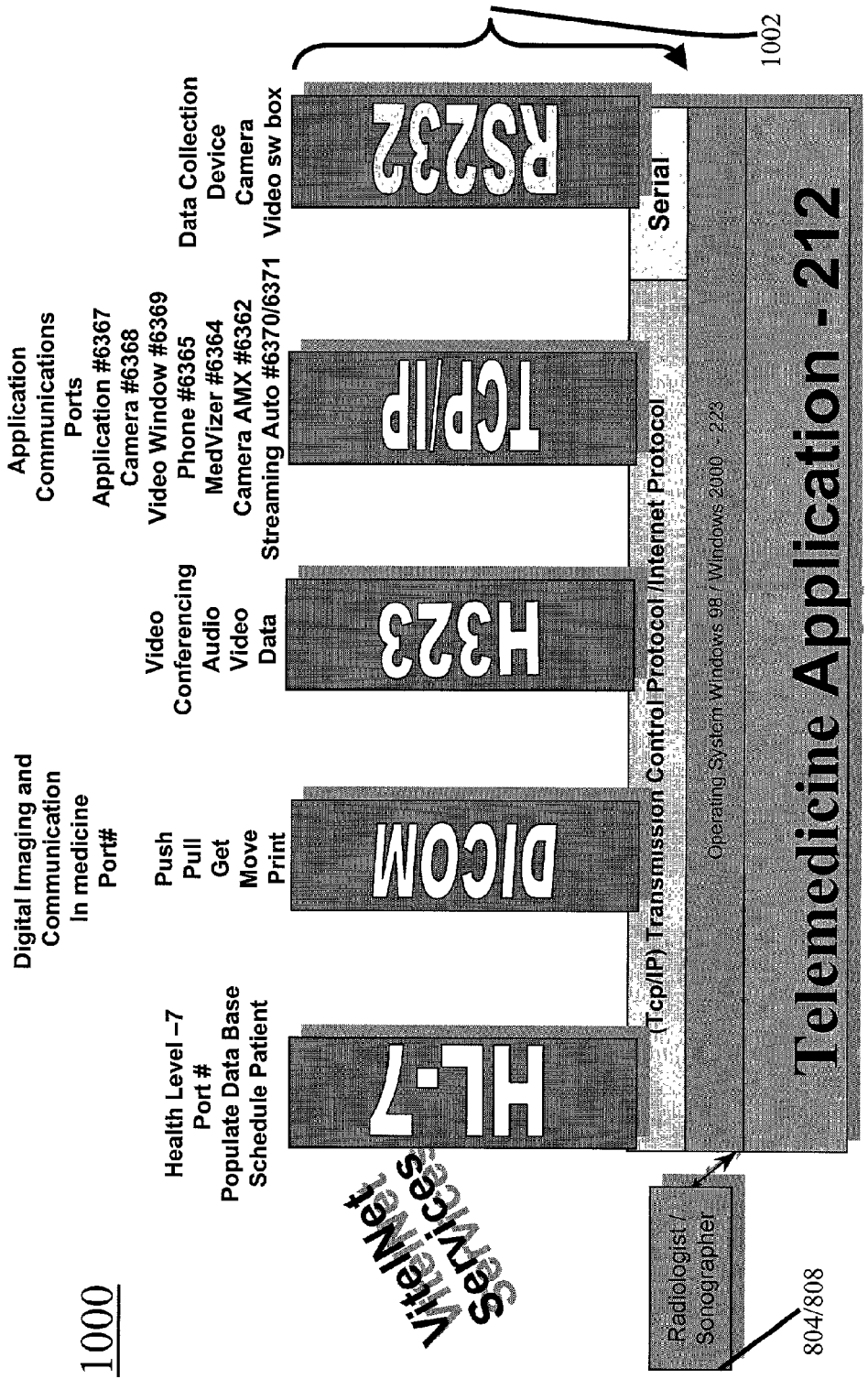

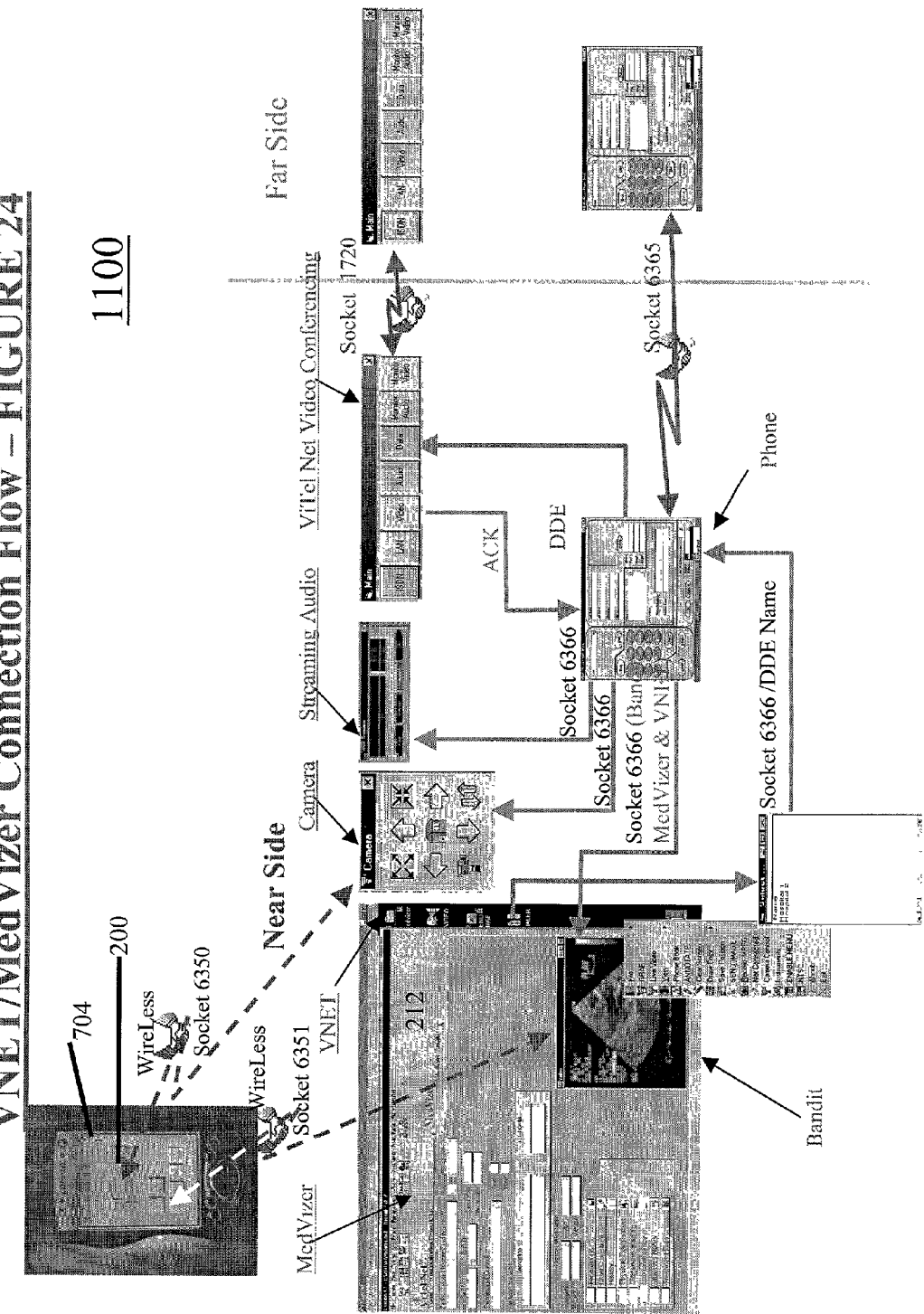

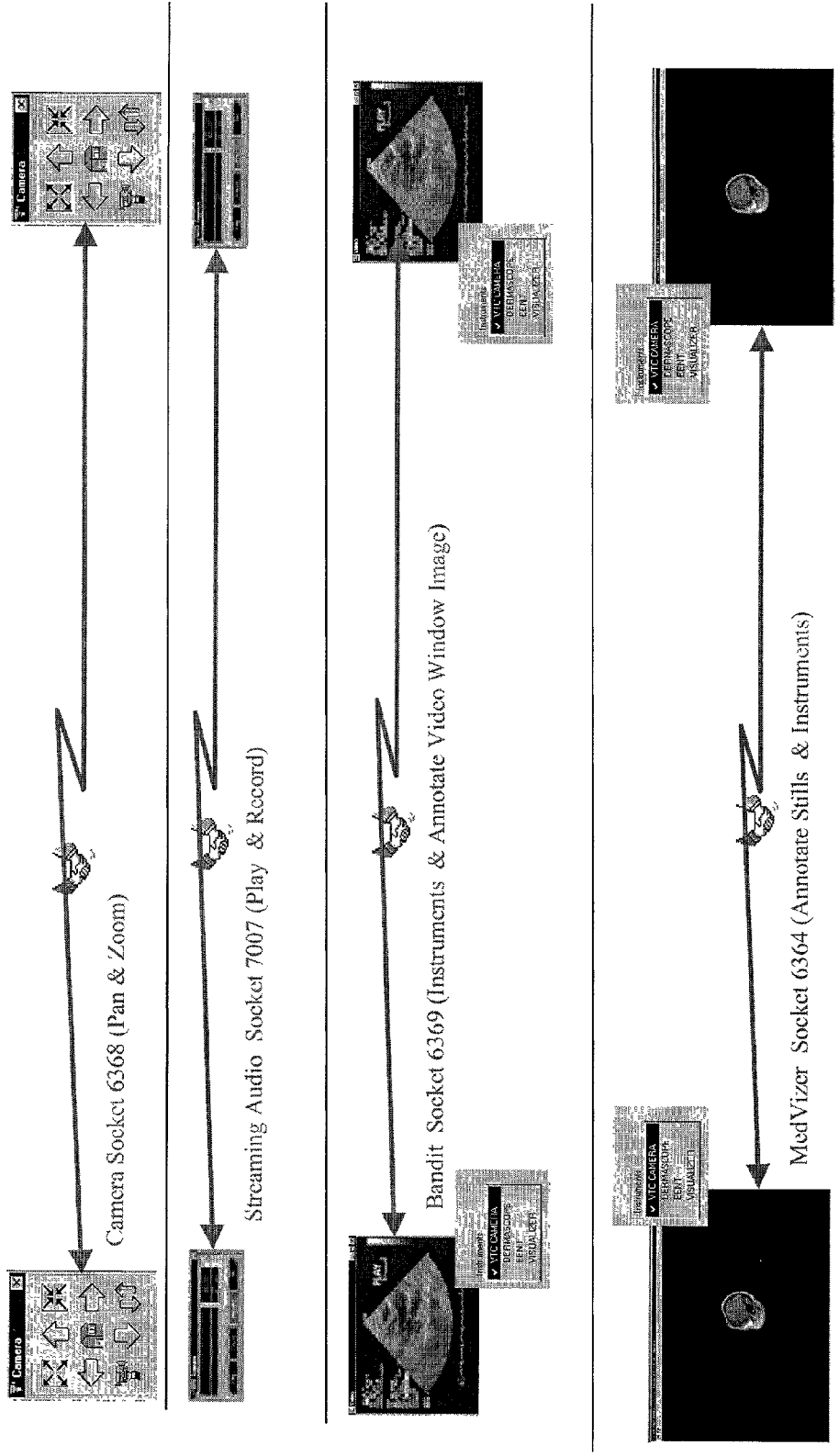

VNET/MedVizer Software – FIGURE 26

1210

ViTelNet

C:\VN\VNET.EXE
C:\VN\Controls.exe

MedVizer

C:\DVDv.exe
C:\VITELNET\VNDEMO.MCF
C:\VITELNET\VNDEMO.MNU
C:\VITELNET\BMPS\VNDEMO.INI

Video Capture

C:\BANDIT\Bandit.EXE
C:\BANDIT\Bandit.ini
C:\BANDIT\Phone.exe
C:\BANDIT\Phone.ini
C:\BANDIT\Phonebk.ph
C:\BANDIT\Remote.exe
C:\BANDIT\Vitelcon.exe

VNET/MedVizer INI File – FIGURE 27A

1300

[Medvizer]
Caption=VitelLINK              Caption that appears in the VNET title bar
lang=                          lang=eng Specifies english language is to be used
                               lang=spa Specifies Spanish language is to be used phpath="c:\bandit\PHONE.EXE @PhoneBook;c:\bandit\joe.ph; /VCON"
                               Used by VNET to determine the location and command line associated with the phone book.
phtopic=Phone|Book             Used by VNET to determine the phone DDE topic dvpath=c:\dv\dv.exe c:\VITELNET\VNDEMO.mcf /hide
                               Use by VNET to determine the location and command line associated with DV dvtopic=DV|Dvision             Used by VNET to determine the DV DDE topic and is used in the DDE initialization process. This is also used
                               during the DDE conversations between applications.

LinkItem=Dvision               Used by VNET as part of the DDE initialization. This is also used during the DDE conversations between
                               applications.

bandit=yes                     Flag used to load bandit. Placing a ' at the beginning of this command disables loading of bandit bdpath=c:\bandit\bandit.exe /HIDE /debug /enabledde /W /dv /optibase
                               Used by VNET to determine the location and command line associated with BANDIT. Command line parameters
                               include;
                               /HIDE - loads the application and hides it.
                               /debug - turns debug on
                               /enabledde - enables bandit to conduct dde conversations. This must be part of the command line when using the
                               socket /W parameter.
                               /W - enable sockets
                               /Optibase enables MPEG encoding from the bandit window.

bdtopic=bandit|bandit          Used by VNET to determine the BANDIT DDE topic and is used in the DDE initialization process. This is
                               also used during the DDE conversations between applications.

VNET/MedVizer INI File- FIGURE 27B

1300

;Control panel for amx ctpath=c:\vn\controls.exe /c1 /hide /w  Used by VNET to determine the location and command line associated with BANDIT.
cttopic=controls|controls  Used by VNET to determine the Controls DDE topic and is used in the DDE initialization process. This is also used during the DDE conversations between applications exit!=yes  When set to yes the video conferencing software will exit without prompting the operator. When this command is disabled a prompt will be presented to the operator prior to exiting.

remdrive=v:  This is the drive letter that will be assigned and mapped when connecting to a remote system.

remcom=2  This is the com port assigned to the camera or the AMX controller is connected to.

[Menu]
Show=NO  Controls the displaying of the VNET button bar. When this command is disable the menu bar will display. When enabled and No follows the equal sign the menu bar will not be displayed.
AOTop=NO  Always On Top - is used to specify if the button bar is always on top are if another form can be displayed over it. When this command is disabled the button bar will always be on top. When enabled the button bar can be covered by another form.

[ports]
@Udp=6366  Broadcast Socket
@Net=6367  VNET to VNET Socket
@Cam=6368  Camera Socket
@Ban=6369  Bandit Socket
@Phn=6365  Phone Socket
@Dvp=6364  MedVizer Socket
@Hcp=6363  Health Socket
@Ctl=6362  Camera Controls AMX
@Spc=6370  Streaming Player Client
@Sps=6371  Streaming Player Server

MedVizer MNU File – FIGURE 28A

WINDOW HEADING Definition - Enter heading to display at top of window.

!     ViTel Net DEMO

COLUMN HEADING Definition - Enter heading to display over search fields.

!Sequence No     Patient ID     SS#

PROMPT LINE Definition - Enter prompt message for user to act on.

!Enter Search Information

FIELD NAME Definitions - Enter Field definitions as follows:
Name,Position,Length,I - "I"=Indexed field (optional)
@DBFLD11,1,28,I
@DBFLD21,18,25,I
@DBFLD20,44,11,I The following specifies the drive letter that basket will be transferred to.

[NIWOT]
_NIWOTCOPY_V_DV_DV_

The following commands enable MedVizer functions and ICONS

_EXIT_
_LOCATE_
_NEXTREC_
_PREVREC_
_FIND_
_ASK_
_ADDREC_
_PickDocument_
_FILEDocument_
_CloseOnExit_
_VideoConferencing_
_RECORDWAVE_
_Scan_
_TwainDevice_
_MainSrhRec_
_MainView_
_VolGen_
_SavePostion_
_volgen_
_savepostion_

252

MedVizer MNU File- FIGURE 28B

_252_

Location and size of the MedVizer Patient Folder

```
_Top_ 690_
_Left_ 4200_
_Height_ 10830_
_Width_ 9960_
```

The following specifies the tab that a specific file is capture to.

```
_.TIF_Tab1_
_.WAV_TAB5_
_.JPG_Tab2_
_.AVI_Tab4_
-.ASF_Tab3_
```

The following turns the list thumbnails on and specifies the size of the thumbnail.

```
[ThumbNail]
Enable=YES
_THUMBNAIL_32_24_
```

The following lines are related to MedVizer's Volume management

```
DOC_R_VNDEMO    AUTO
LST_R_VNDEMO    AUTO
_PTH_
_PTH_
_PTH_
_CPY_R_VNDEMO    AUTO
[
```

```
TOOL]
XRAY=ACCUSOFT
NUMXRAYS=9
THUMBWIDTH=80
THUMBHEIGHT=100
THUMBCOUNT=6
THUMBSPACE=20
THUMBFRAME=15
THUMBROWS=2
TOOLBARS=SMALL
AUTOVIEWRATE=10
MAGSMALL=100
MAGMEDIUM=200
MAGLARGE=300
MAGMAG=2
MENUHEIGHT=16
MENUFONT=8
SCANDPI=75
SCANBITS=8
SCANOPT1=75
SCANOPT2=150
XRAYBGCOLOR=00000000
SHOW=YES
DATABASE=R:\VITELNET\VNDEMO.dbf
```

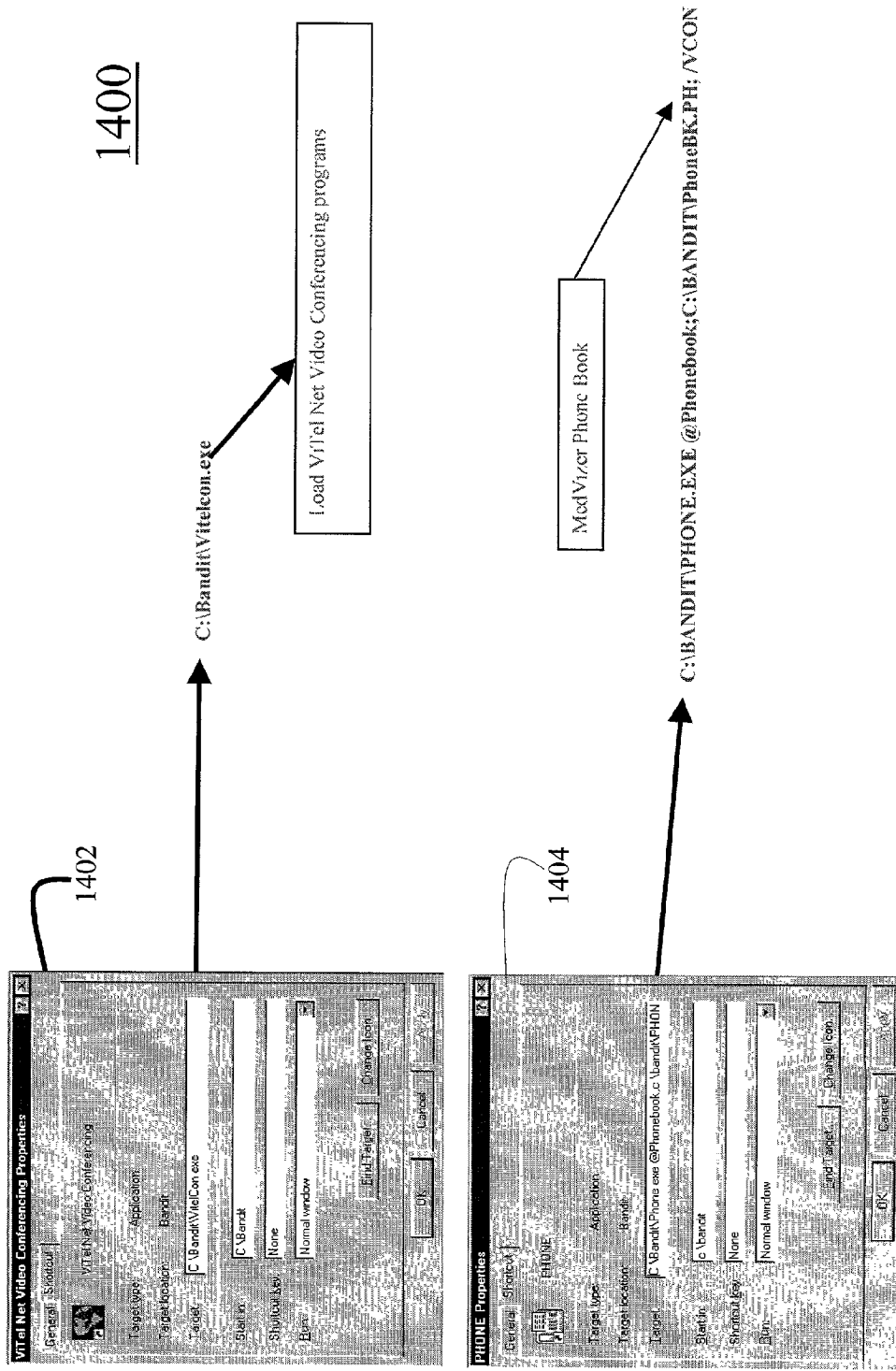

VNET Properties – FIGURE 30
1500
Initializes the system based on information acquired from the VNDEMO.INI file.
Configures the Desk Top
    Creates Menu Bar
        Size and location
        Buttons (BMP files located in \VitelNet\BMPS directory
        Establishes MedVizer Window size and location
Loads MedVizer (DV.exe)
Loads Bandit.exe
Established DDE links
Controls program interaction
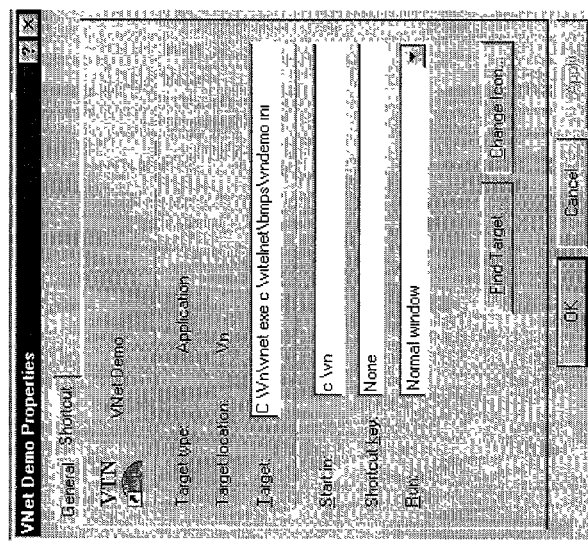

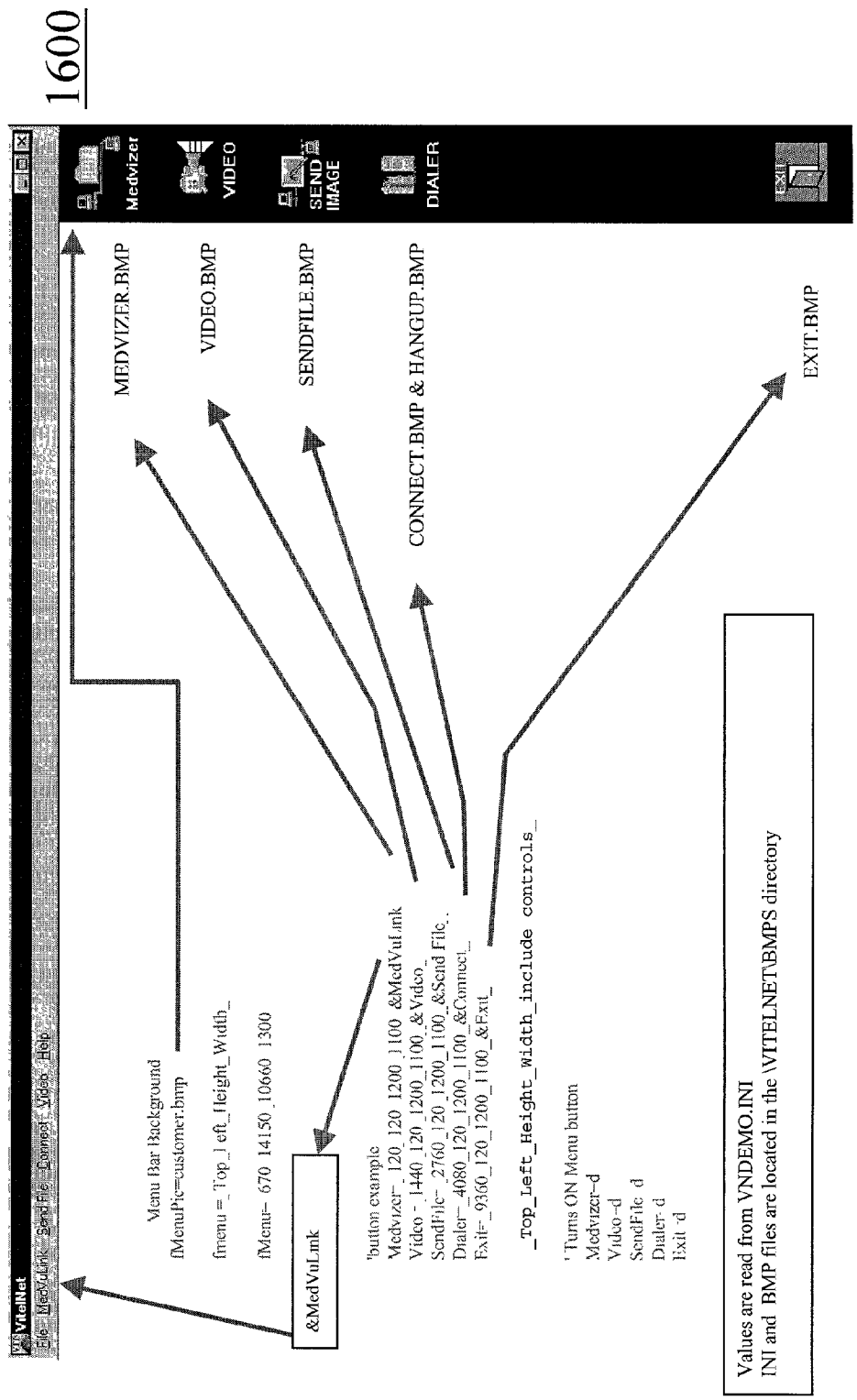

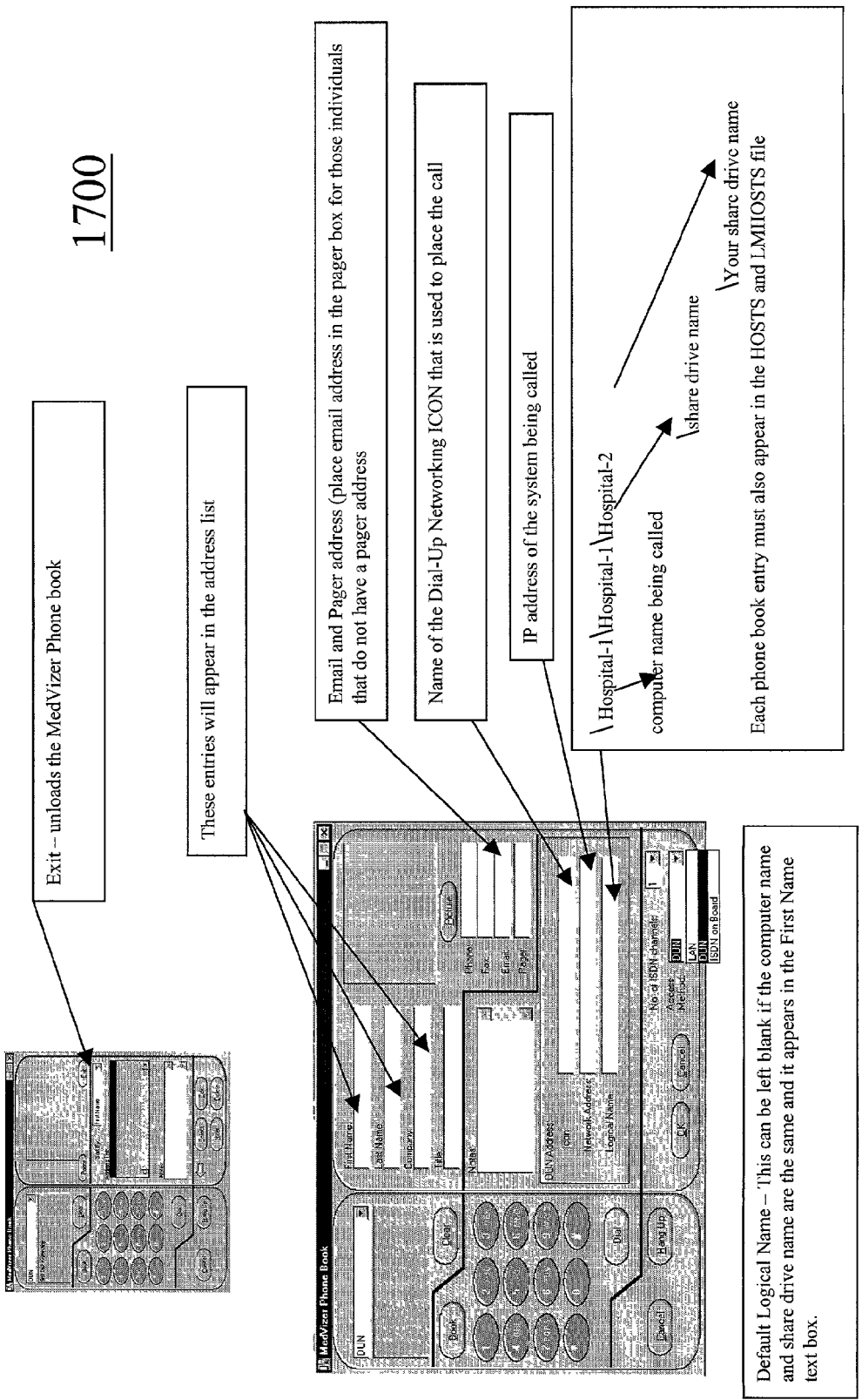

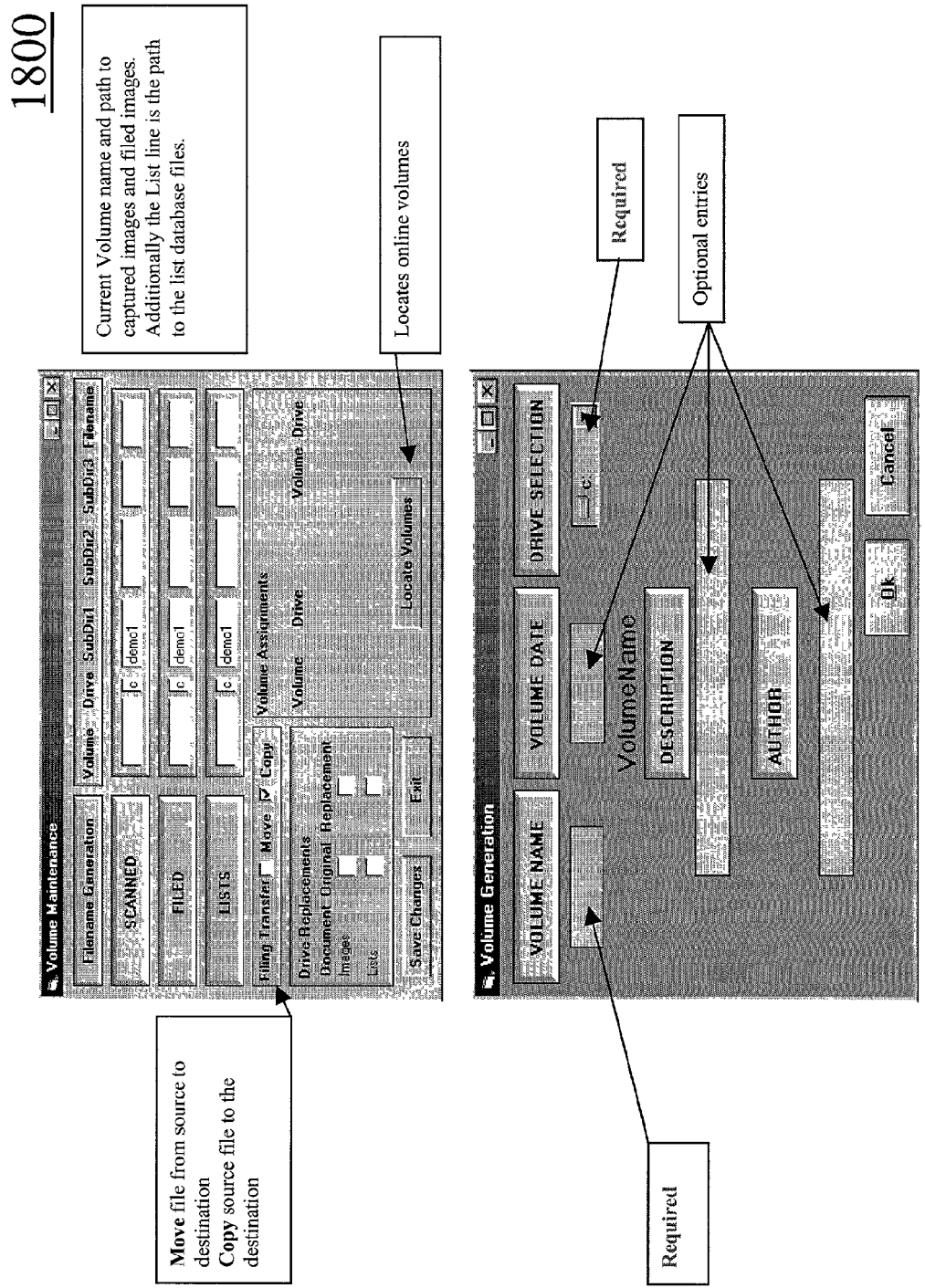
Volume Information & Generation – FIGURE 33

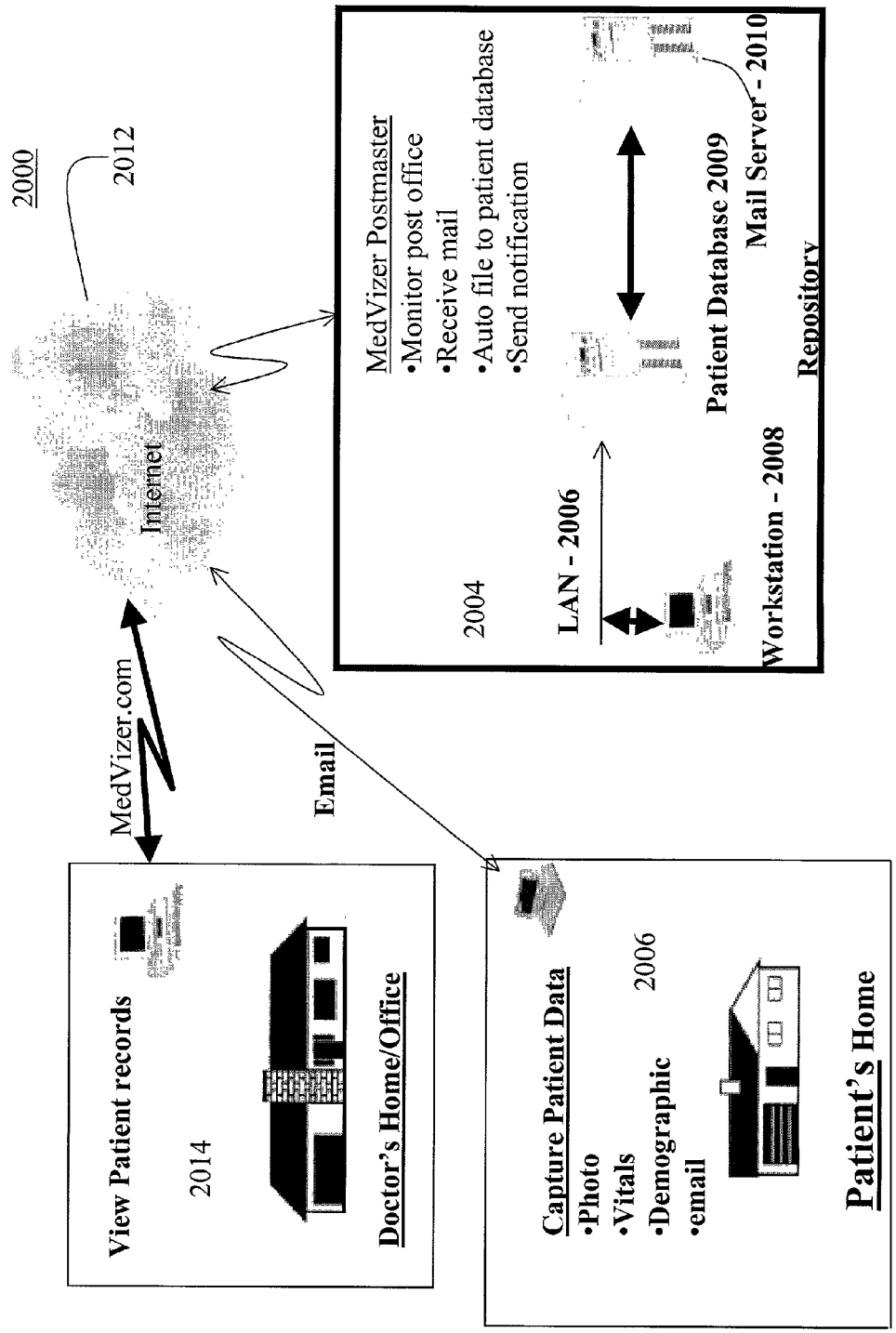

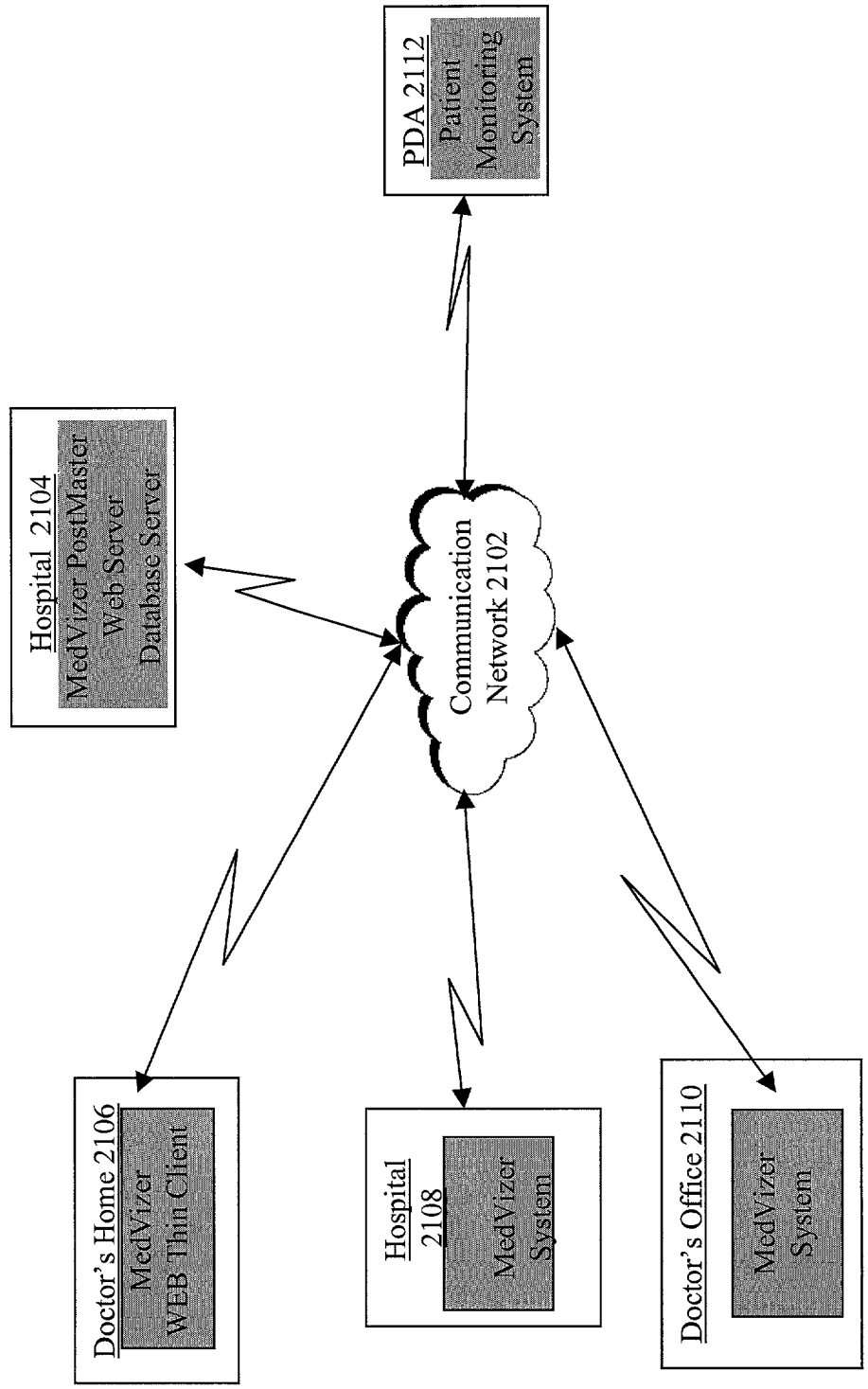

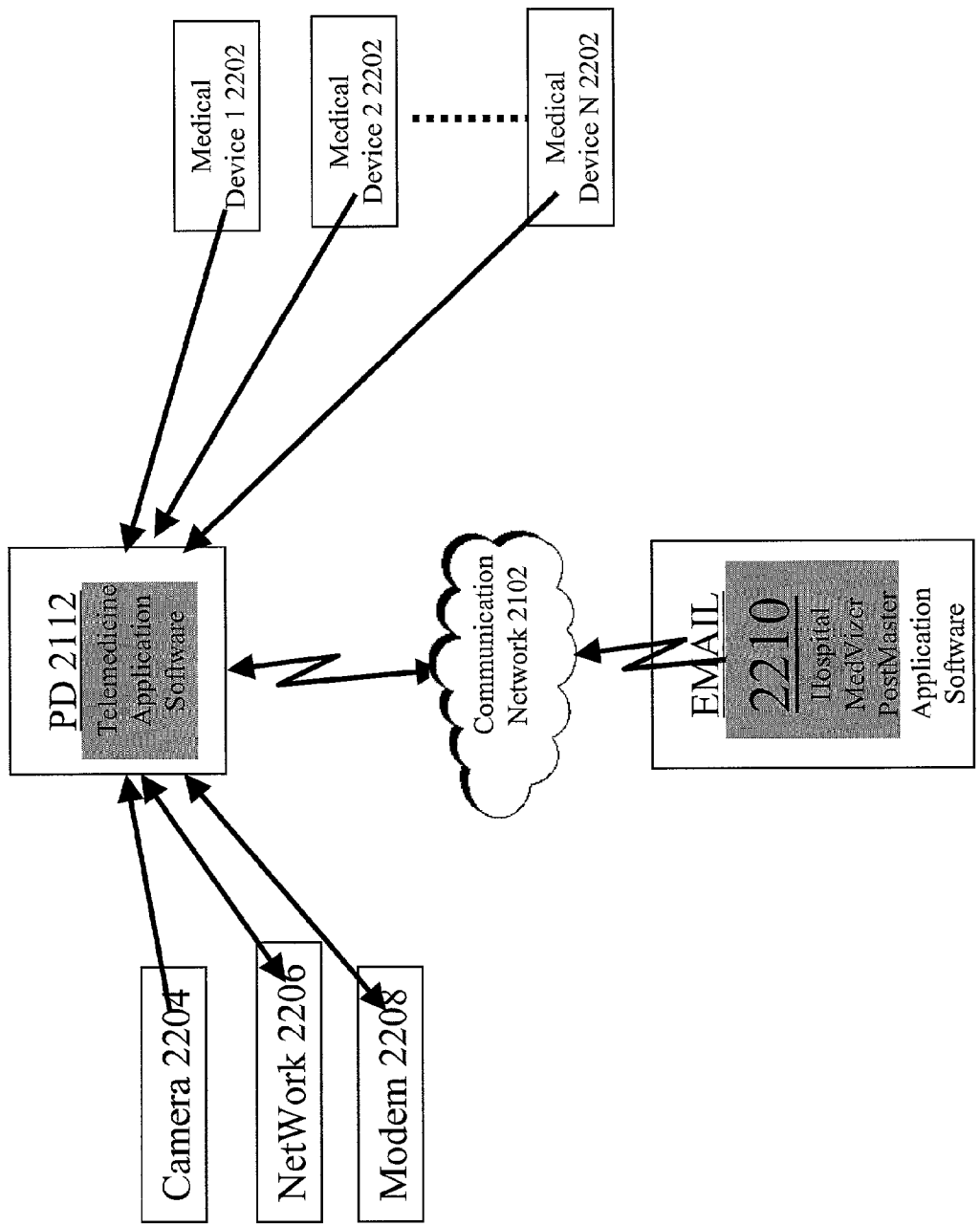

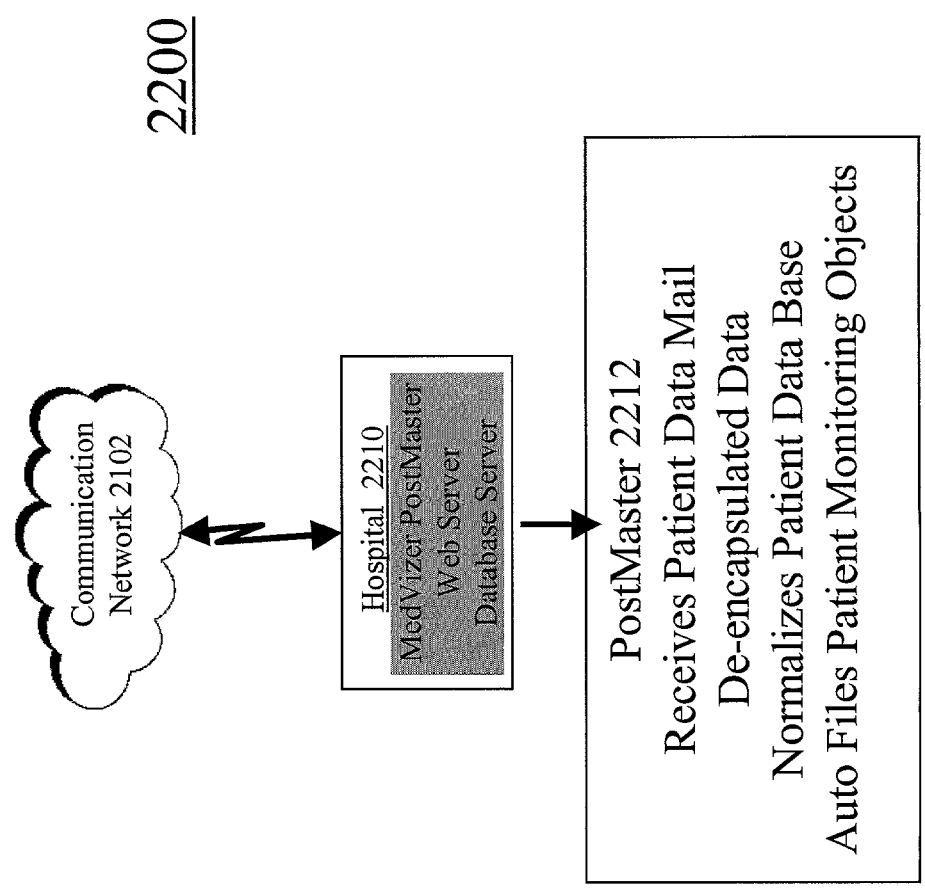
PD Complete Home Monitoring System – FIGURE 37B

2212

METHOD, APPARATUS, AND MEDIUM USING A MASTER CONTROL FILE FOR COMPUTER SOFTWARE INTEROPERABILITY BETWEEN DISPARATE OPERATING SYSTEMS

CROSS-REFERENCE TO RELATED APPLICATIONS

This application is related to, and claims priority to, Provisional Application U.S. Ser. No. 60/236,726, filed Oct. 2, 2000, the contents of which are incorporated herein by reference.

This application is also related to, and claims priority to, Provisional Application U.S. Ser. No. 60/221,558, filed Jul. 28, 2000, the contents of which are incorporated herein by reference.

BACKGROUND OF THE INVENTION

1. Field of the Invention

The present invention relates to interoperability between computer systems, and, more particularly, to providing interoperability between computer systems and organizations by using a middleware master control file. Moreover, the present invention relates generally to medical Pocket Devices and, in particular, to methods which support a wide variety of measurement, collection, communication, and analysis functions.

2. Description of the Related Art

Computer-based medical information systems are known in the art. These computer-based medical information systems include medical information tools categorized as: (1) data collection devices, or (2) hospital information systems. The hospital information systems include input, storage, and retrieval of patient records and Picture Archive and Communication Systems (or PACS).

An example of application software corresponding to medical information software 10 is shown in FIG. 1. As shown in FIG. 1, the medical information software 10 creates and maintains a folder with patient demographics and image files, in the format of a medical record 12. The medical record 12 is created using input data from a variety of sources, including a hospital information system 16, a photographer 18, a database 20, PACS image acquisition 22 through a DICOM/Push, and an MPG file 24. Images from the PACS image acquisition are displayed on a physician workstation 26, through a DICOM/Pull using TCP/IP.

FIG. 2 shows a local area network (LAN) configuration 30 of the medical information system 10 shown in FIG. 1. As shown in FIG. 2, data including the patient database files 32 and the volume—images objects that have been filed and captured 34 are stored on server 36. This data is transmitted to the server 36 over a local area network 38 after acquisition from a variety of instruments 40, including dermascopes, endoscopes, otoscopes, ophthalmoscopes, stethoscopes, microscopes, echocardiograms, ultrasound, and MRI/CT. Moreover, this data may include patient demographic information entered using computer 42. This data, once stored on the server 36, can be displayed on a physician workstation 22 or printed on a printer 44.

A typical environment for the local area network configuration 30 would include the computer 42 executing the WINDOWS 98 operating system, the local area network 38 including TCP/IP, share name, LMHOSTS, and HOSTS, and a startup using the MEDVIZER Phone and VITEL NET video conferencing. That is, VITEL NET application software 10 being executed by a local area network configuration 30, through telephone lines (POTS), through ISDN lines, through T-1 lines, and over satellite is known in the art.

Although experts in the two fields of data collection devices and hospital information systems have been working to form standards within their respective fields, deficiencies remain. Also, personnel in the medical information systems industry have been much less successful in developing a common set of commands and protocols to allow concurrent operation within the various categories of medical information tools.

Despite a tidal wave of new technologies, a consistent trend towards proprietary communications languages, protocols, and stand-alone medical systems sustains an unacceptable requirement for redundant systems, training, and excessive capital equipment costs. This cost is born disproportionately by the customer where operational requirements span a great diversity of needs, including special operations in remote medical care.

Moreover, confusion arises in attempting to make computer systems with disparate proprietary communications languages, protocols, and stand-alone medical systems communicate with each other. The current confusion in medical communications supports the manufacturers of large and expensive systems, but interferes with efficient and cost-effective healthcare delivery.

There is a need for a common set of medical information communications protocols, or common standards. The use of a common set of medical information communications protocols would improve healthcare delivery within the private sector while markedly reducing the costs associated with healthcare delivery. Moreover, the development of common standards could be one of the most important breakthroughs in health care in the coming years.

One way of providing a common set of medical information communications protocols, or common standards, is by an architecture which includes the use of a master control file. A master control file (or MCF) is middleware software storing information which, when read by a computer program referred to as an engine, provides an interface between an application program and the WINDOWS operating system. The master control file (or MCF) provides an open, interoperable, platform and language independent distributed (MCF) architecture. This approach has been enormously successful and has been adopted by numerous large firms around the world as the basic architecture for their complex Patient Record Information systems. This infrastructure provides a great deal of power, scalability, and interoperability.

An example of an architecture 110 using a master control file is shown in FIG. 3. As shown in the architecture 110 of FIG. 3, an application program 112 (such as a VITEL NET Application) interfaces to a master control file (MCF) 114, as well as to an MNU 116, and a database 118. The MCF 114, the MNU 116, and the database 118 are then read by an engine 120 (such as a VITEL NET engine), which interfaces to the WINDOWS operating system 128 through the WN32 API 122, OCX files 124, and DLL files 126. The operating system 128 includes functions such as a virtual memory manager 130, a file system manager 132, and a configuration manager 134, as well as the kernel 136. The operating system 128 then interfaces to device drivers 138, which interface to hardware 140.

The functionality and interfacing provided in the engine 120 corresponds to the operating system 128 to which the engine 120 is interfacing. The use of a VITEL NET engine 120 corresponding to the WINDOWS operating system 128 and the WINDOWS NT operating system 128 is known in the art. A typical programming language in which the engine 120 is written is VISUAL BASIC.

With the use of engine 120, the master control file 114 and the application programs 112 are not required to change when ported between the WINDOWS operating system 128 and the WINDOWS NT operating system 128.

MEDVIZER Technology Overview

An overview of a medical information system 10 is now presented.

VITEL NET's core technology revolves around FDA-cleared development software called the Dvision Toolbox (or master control file (MCF)), and the MEDVIZER (Medicine Visualizer) Engine. The Dvision Toolbox utilizes a set of tools and programs that allow VITEL NET to create, modify, and manage multi-media databases and applications in a programmer-less environment. The MEDVIZER Engine is a set of programs that provides the specific functionalities for the applications created with the Dvision Toolbox. The VITEL NET Division Toolbox is known in the art and has proven to be a foundational technology on which to build and launch customizable products and enterprise-wide solutions. The Dvision Toolbox is the workbench on which solutions are designed and constructed for customers in a programmer-less environment.

Specific clinical products in areas such as General Telemedicine, Teleradiology, Teleultrasound, Telecardiology, Post Acute Care and Home Care, offered as turnkey solutions are known in the art, and each clinical is customized as a value-added service to address the health care requirements and needed specifications of users.

Open-architecture, and scalable telemedicine products and services are known in the art, as are enterprise-wide solutions for users, including ensuring security of data, infrastructure scalability, integration with legacy systems and the ability to capture and present information without dependence upon time or place.

Moreover, the complexities of today's health care marketplace are burgeoning. An increasingly mobile society, coupled with changes in care delivery protocols, legal regulations (such as HIPPA), and the all too fluid business landscape, present significant challenges to most health care providers and the vendors who serve them.

Also known in the are the following functions and features of the VITEL NET Dvision Toolbox and MEDVIZER Engine, which allow rapid tailoring of products to meet specific users' precise requirements. VITEL NET's core technology enables workflow that allows each patient record to be tracked from start to finish. Customized operator interfaces that are targeted specifically for the individual phases in the workflow are created in a programmer-less environment and yield a complete solution.

Moreover, VITEL NET's products are integrated with existing legacy hospital, radiology or clinical information systems, enabling users to leverage existing investments and the delivery of effective image distribution and management solutions.

In addition, the medical information system 10 enables consultations with remote facilities using store-and-forward and/or real-time modes, all of which are compatible with any conventional telecommunication system, including POTS, ISDN, T-1, Satellite, and wireless Internet/LAN.

Further, the medical information system 10 offers key enterprise technologies like the versatile MedVizer Postmaster. The MedVizer Postmaster Server receives patient data, updates the central database, routes the information to the intended clinician, and can send alerts indicating that clinical data are waiting for review.

Moreover, the medical information system 10 provides information security. VITEL NET's Security Services module meets or exceeds today's demanding the HIPPA security and information tracking requirements.

Also, the medical information system 10 provides the technical and clinical expertise to assure that the solution delivered is designed to meet specific user requirements and operates reliably with the user's existing systems.

Also known in the art are VITEL NET's Enterprise Solution Components, including:

MedVizer Postmaster
MedVizer Desktop Manager
MedVizer PACS Gateway/DICOM Manager
MedVizer-Enabled Web-Browser
Telephony Manager
Collaboration Manager (Camera/Device Control & Annotation)
Chat Manager
Data Manager Services
Workflow Services
Folder Management
Report Generator
Image Manipulation Services
Enterprise Security Manager
Volume Management Services
Bar Code Services
Device Capture Manager
Videoconferencing
Interface Manager (HL7, DICOM 3.0)
Store and Forward Exchange Services
Multi-form Management Services
C.O.L.D. (computer output to laser disk)

What is needed is a master control file and an engine which enable an application program to be ported to a hand-held device or used over the Internet, without requiring change to the application program, and which enable interoperability of the application program between disparate operating systems.

Moreover, there exists a need for comprehensive physiological monitoring in portable and remote settings. Current systems are generally large, costly, and inflexible. Pocket Devices can digitized, encapsulated, and routed through a complex digital network under programmed control there by offering a truly universal data exchange functions.

At the same time, in the computer industry there has been a movement toward system interoperability through open systems protocols. This movement is being driven by TCP/IP, followed by Windows CE and now applications level protocols SMTP and MAPI. These protocols standards have allowed interoperability between computers using different operating systems, hardware platforms, and applications suites. Within the Government and industry these data transfer protocols, mostly oriented towards transmission and/or sharing of images and documents have substantially improved the usefulness of office and home Computers' with respect to medical PD, however, such support for multiple platforms or distributed, object-oriented collection and analysis architectures for multiple data types do not yet exist.

SUMMARY OF THE INVENTION

The present invention solves the above-mentioned problems of the related art.

More particularly, the master control file of the present invention solves the above-mentioned interoperability problems, and provides for a set of common standards to which systems and components may adhere and thus become interoperable.

The master control file of the present invention comprises middleware software, and is referred to as VITEL NET Master Control File (MCF) middleware. The VITEL NET Master Control File (MCF) middleware provides full interoperability between disparate systems (i.e., systems running operating systems such as WINDOWS CE, WINDOWS NT, WINDOWS and the Internet) and organizations.

The VITELNET Master Control File is discussed in Provisional Application U.S. Ser. No. 60/236,726, filed Oct. 2, 2000, the contents of which are incorporated herein by reference.

Moreover, the master control file, and engines, of the present invention enable a medical information system (such as offered by VITEL NET) to include wireless communications and Personal Desktop Assistants (PDAs) as part of a diverse range of telemedicine applications.

Another aspect of the present invention satisfies the need for a general-purpose, Palm device, low-cost system which provides comprehensive physiological data collection, with extensive data object oriented programmability and configurable for a variety of medical data collection applications. Medical devices can be digitized from a common point of contact. A general-purpose data routing and encapsulation architecture supports input tagging and standardized routing through modern packet switch networks, including the Internet, From one of multiple points of origin or patients, to one or multiple points of data analysis for physician review. The preferred architecture further supports multiple-site, and real-time data collection, routing, and viewing (or slower than real-time processes when communications infrastructure is slower than the data collection rate). Routing and viewing stations allow for the insertion of automated analysis routines to aid in data encoding, analysis, viewing, and diagnosis.

A pocket device global medical records system is discussed in Provisional Application U.S. Ser. No. 60/221,558, filed Jul. 28, 2000, the contents of which are incorporated herein by reference.

Additional aspects and advantages of the invention will be set forth in part in the description which follows and, in part, will be obvious from the description, or may be learned by practice of the invention.

BRIEF DESCRIPTION OF THE DRAWINGS

These and other objects and advantages of the invention will become apparent and more readily appreciated from the following description of the preferred embodiments, taken in conjunction with the accompanying drawings of which:

FIG. 11A and FIG. 11B show server side and client side master control files of the present invention.

FIG. 12 shows a process of the present invention.

FIG. 13 shows screens of the master control file.

FIG. 14 shows master control file field names.

FIG. 17 shows master control file field locations and attributes.

FIG. 19 shows another aspect of MEDVIZER object storage and retrieval.

FIG. 20 shows a secure wireless telemedicine enterprise system.

FIG. 21 shows a telemedicine system.

FIG. 22 shows a VITEL NET telemedicine system.

FIG. 23 shows communications architectures.

FIG. 24 shows connection flow.

FIG. 25 shows remote TCP/IP functions.

FIG. 26 shows VNET/MEDVIZER software.

FIG. 27A and FIG. 27B show a VNET/MEDVIZER INI file.

FIG. 28A and FIG. 28B show a MEDVIZER MNU file 252.

FIG. 29 shows a system start up group 1400, including establishing VITEL NET video conferencing properties 1402 and PHONE properties 1404.

FIG. 30 shows VNET properties 1500.

FIG. 31 shows the VNET desktop 1600.

FIG. 32 shows the MEDVIZER PHONE BOOK 1700.

FIG. 33 shows the volume information and generation 1800.

FIG. 35 shows a global medical records system.

FIG. 36 shows a pocket device complete home monitoring system.

FIG. 37A and FIG. 37B show a pocket device home monitoring system.

DESCRIPTION OF THE PREFERRED EMBODIMENTS

Figure 1:
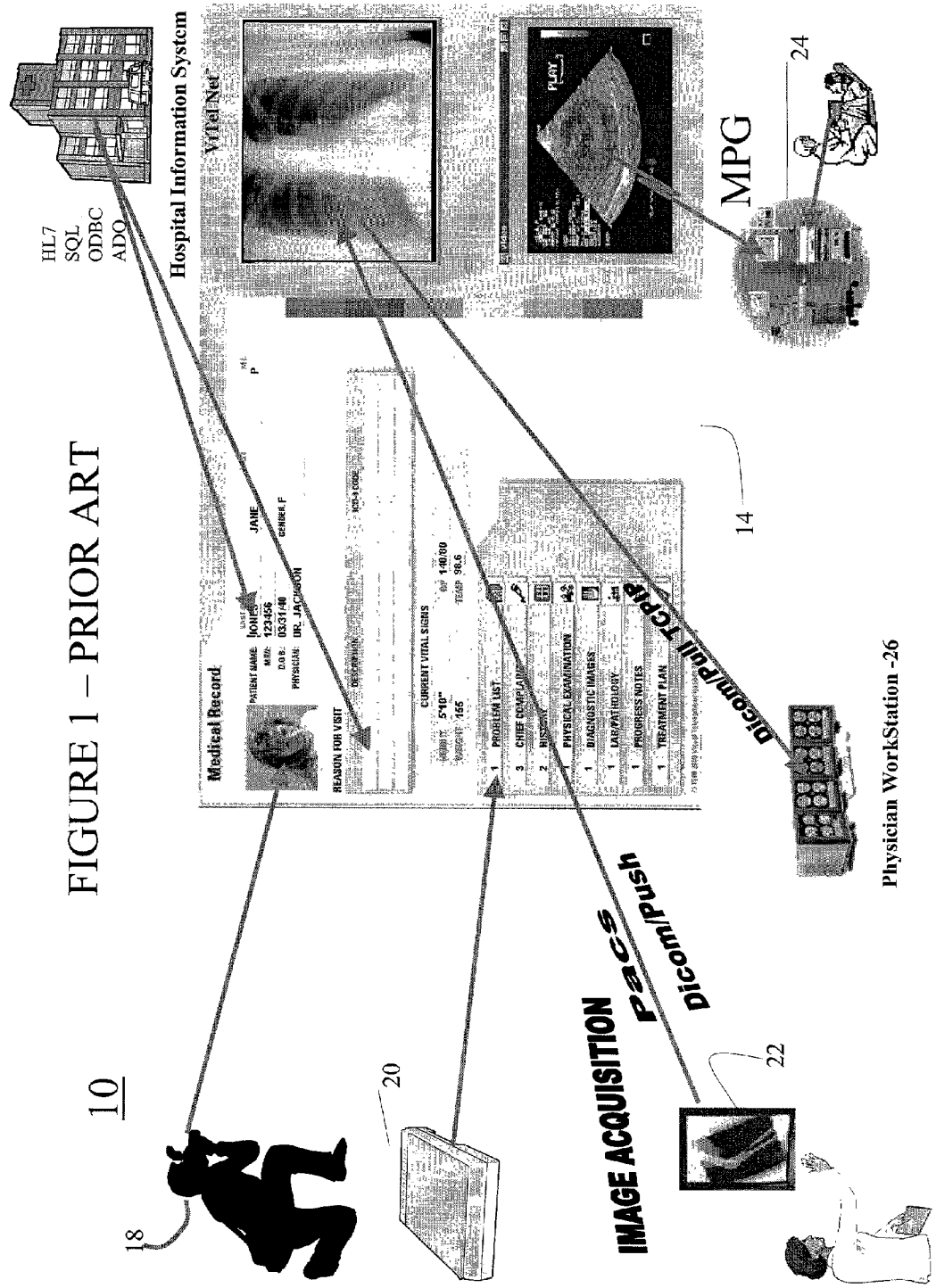
FIG. 1 shows medical information software of the prior art.
Figure 2:
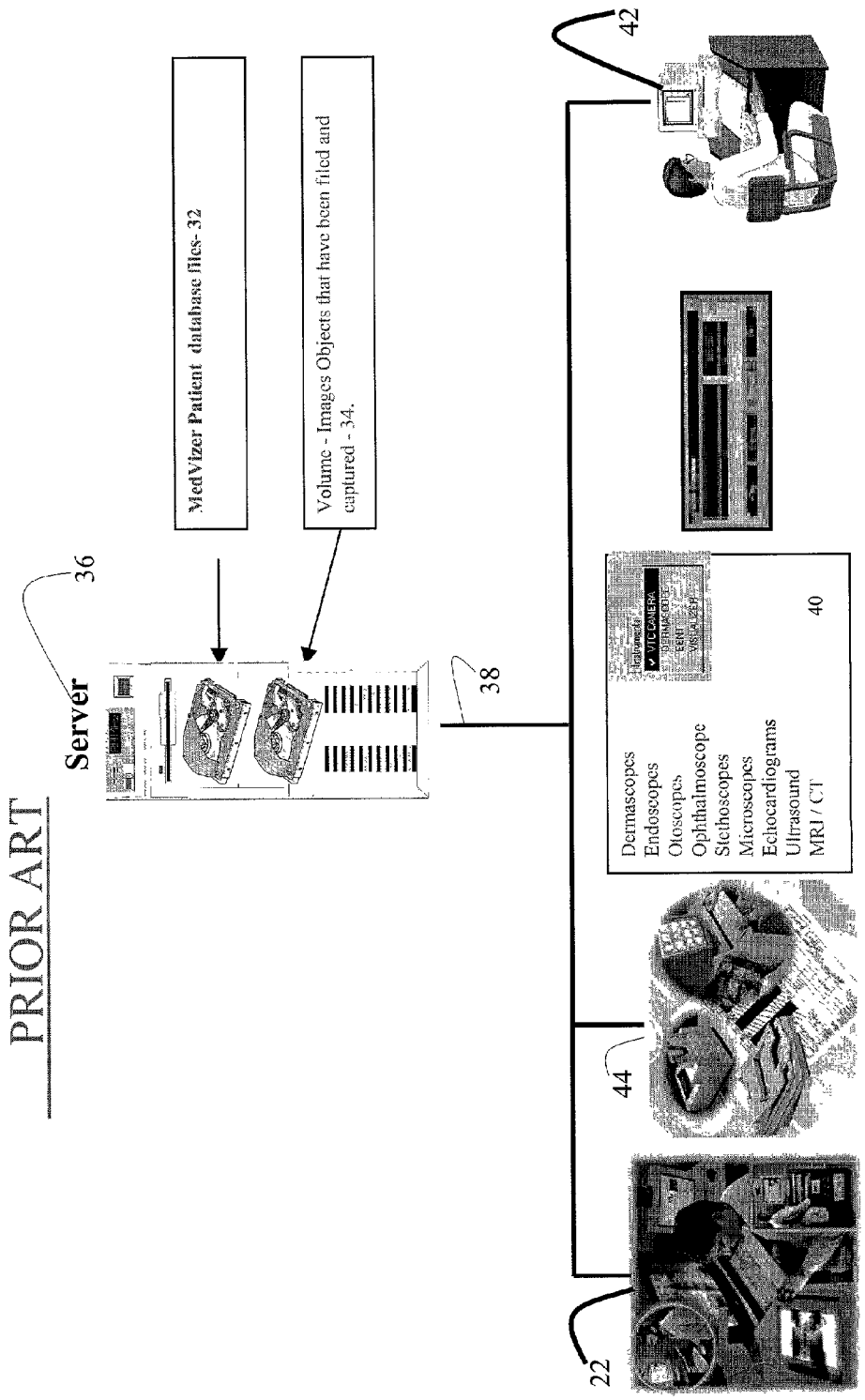
FIG. 2 shows a local area network (LAN) configuration 30 of the medical information system 10 shown in FIG. 1.
Figure 3:
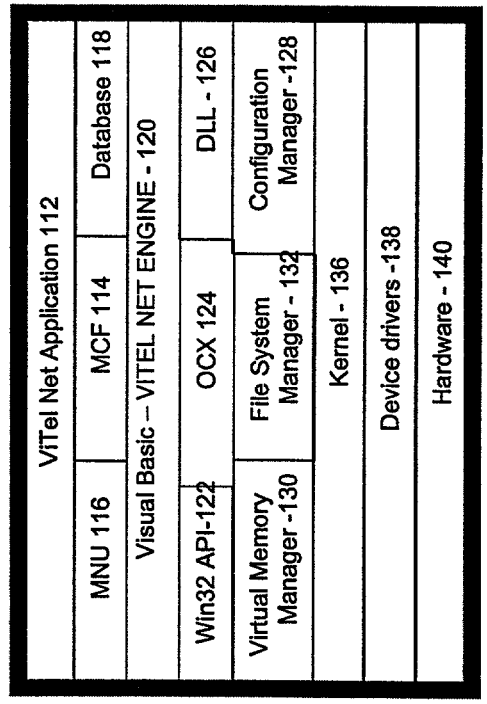
FIG. 3 shows an example of an architecture using a master control file of the prior art.

Reference will now made in detail to the present preferred embodiments of the present invention, examples of which are illustrated in the accompanying drawings, wherein like reference numerals refer to the like elements throughout. The embodiments are described below in order to explain the present invention by referring to the figures.

The master control file of the present invention is useful in a variety of computing environments, including Internet-based computing (in which a Web engine is used), thin client computing, personal digital assistant (PDA) computing (including POCKET PC/WINDOWS CE systems), networked computing (including WINDOWS 98, WINDOWS 2000, and WINDOWS NT), and standalone computing.

Figure 4:
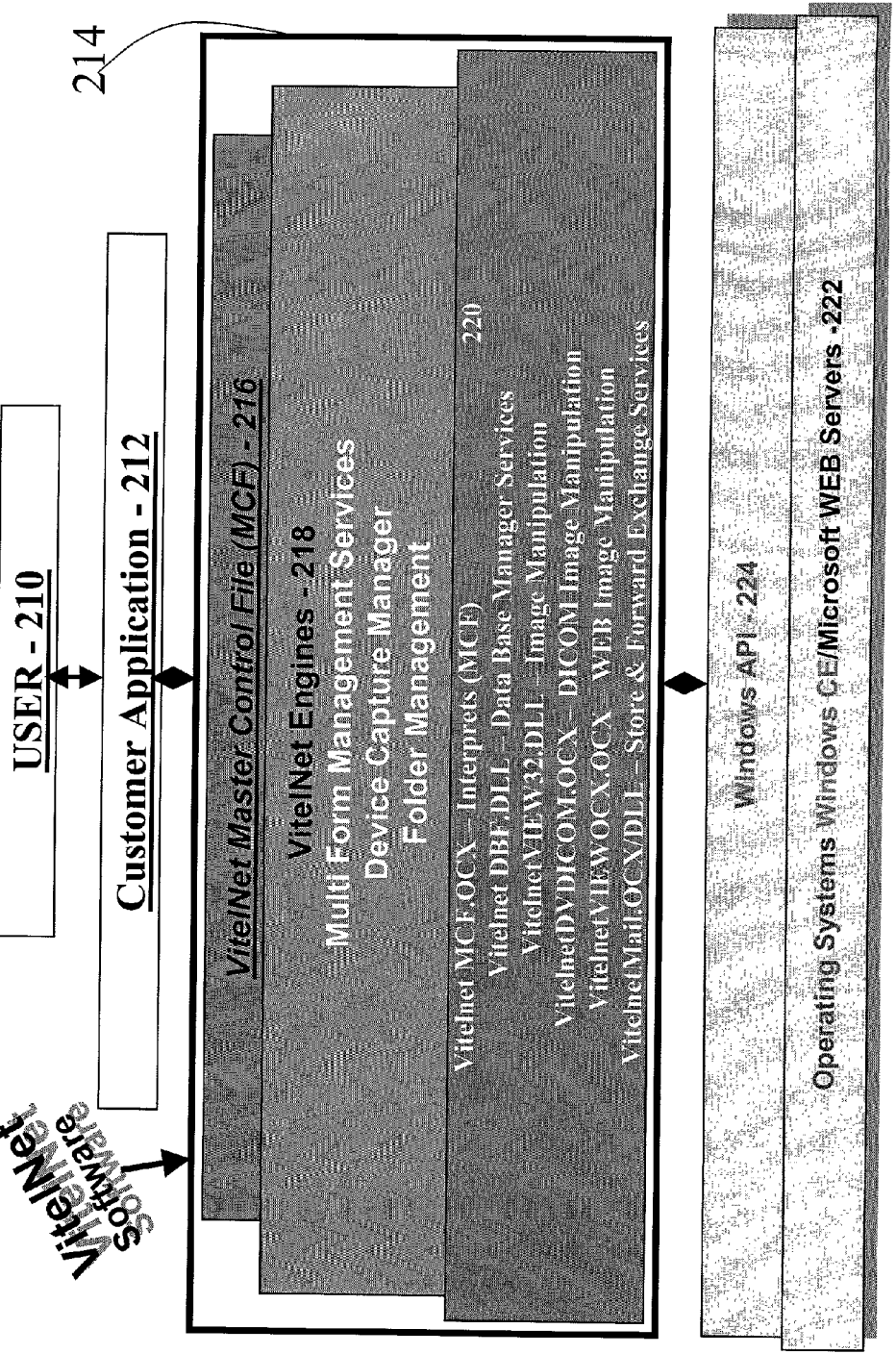
FIG. 4 is an overview of an application architecture 200 of the present invention.

FIG. 4 is an overview of an application architecture 200 of the present invention. In the application architecture 200 of the present invention, a user 210 interfaces with application software 212 (such as VITEL NET medical application software). The application software (or customer application) 212 then interfaces with portability enabling software 214 of the present invention. The portability enabling software 214 of the present invention comprises a master control file 216, engines 218, and support files 220 such as OCX and DLL files.

Then engines 218, which correspond to particular operating systems, provide multi-form management services, device capture manager, and folder management. The support files 220 include (for example):

Vitelnet MCF.OCX, which interprets the master control file 216;

Vitelnet DBF.DLL, corresponding to database manager services;

Vitelnet VIEW32.DLL, corresponding to image manipulation;

Vitelnet DVDICOM.OCX, corresponding to DICOM image manipulation;

VitelnetVIEWOCX.OCX, corresponding to WEB image manipulation; and

VitelnetMail.OCX/DLL, providing store and forward exchange services.

The portability enabling software 214 of the present invention then interfaces to the operating system 222 through an application program interface (API) known in the art and corresponding to the particular operating system 222.

Examples of operating systems 222 to which the portability enabling software 214 of the present invention interfaces include WINDOWS CE and MICROSOFT WEB SERVERS.

The portability enabling software 214 of the present invention isolates the customer application 212 from the operating system 222 and enables portability of the customer application 212 between disparate operating systems (including WINDOWS CE and MICROSOFT WEB SERVERS) without requiring software modifications to the customer application 212.

Within the portability enabling software 214 of the present invention, the master control file 216 does not require changes to support the customer application 212 when ported between disparate systems. The engines 218 and the support files 220, though, are customized to support disparate operating systems 222 through the corresponding APIs 224. That is, the engines 218 and the support files 220 are customized to interface with disparate APIs 224.

Figure 5:
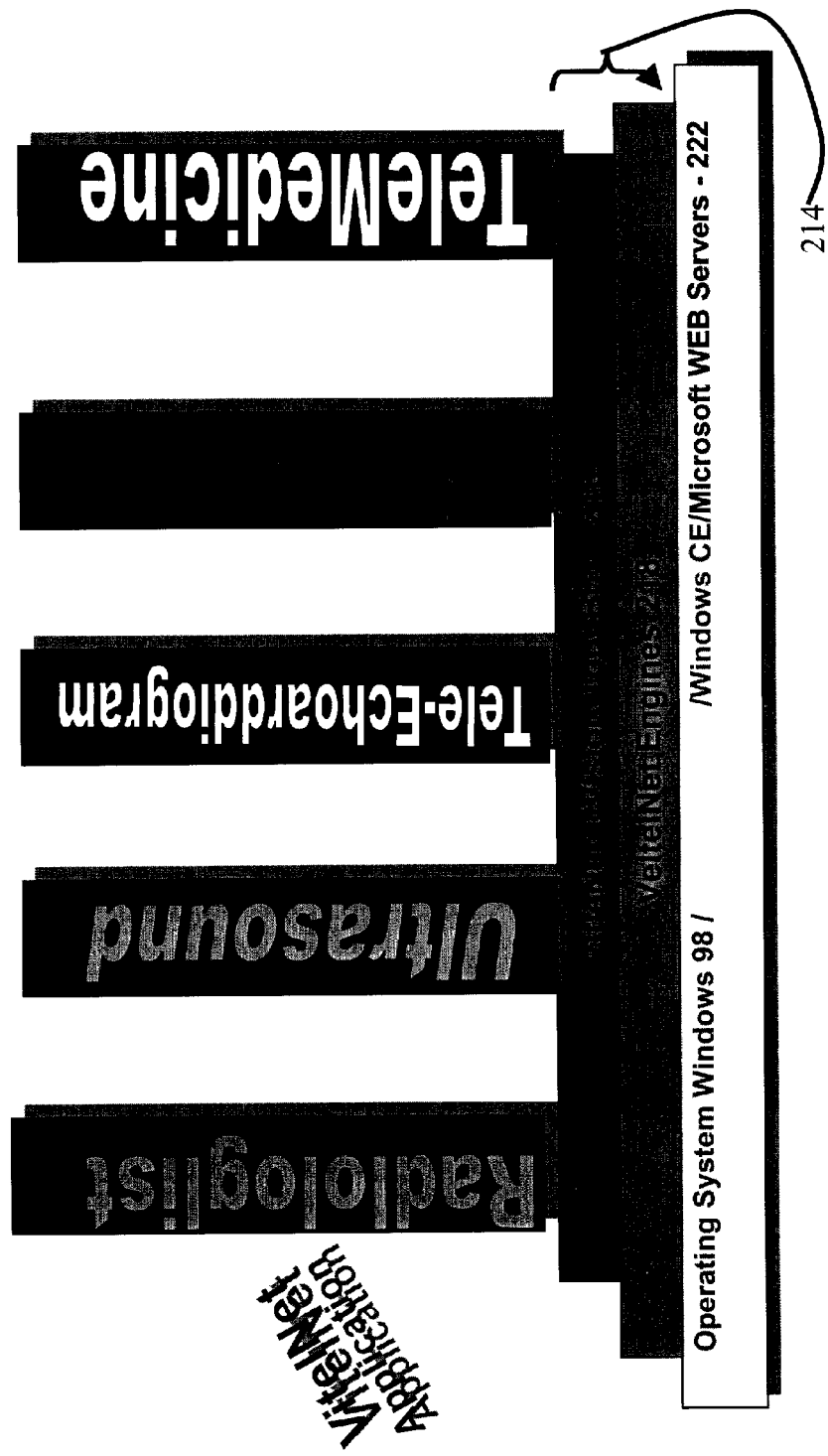
FIG. 5 shows an application architecture of the present invention.

That is, as shown in FIG. 5, the portability enabling software 14 of the present invention enables customer applications 212 such as radiologist 212-1, ultrasound 212-2, tele-echocardiogram 212-3, financial 212-4, and telemedicine 212-5 to be ported between operating systems 222 including WINDOWS 98, WINDOWS 2000, WINDOWS CE, and MICROSOFT WEB SERVERS. Porting customer applications 212 between WINDOWS 98 and WINDOWS 2000 using the master control file 214 and engines corresponding to WINDOWS 98 and WINDOWS 2000 (that is, interfacing to WIN32 API) is known in the art.

Interfacing by the engine to WINDOWS CE (that is, interfacing of the application software to the API corresponding to WINDOWS CE, CEWIN32API), using the master control file and an engine is an aspect of the present invention. Providing the ability for the application software to be executed over the Internet using the master control file and an engine, which is another aspect of the present invention, involves interfacing by the engine to an API resident on the target computer, such as WINNT32 API or CEWIN32API).

Figure 6:
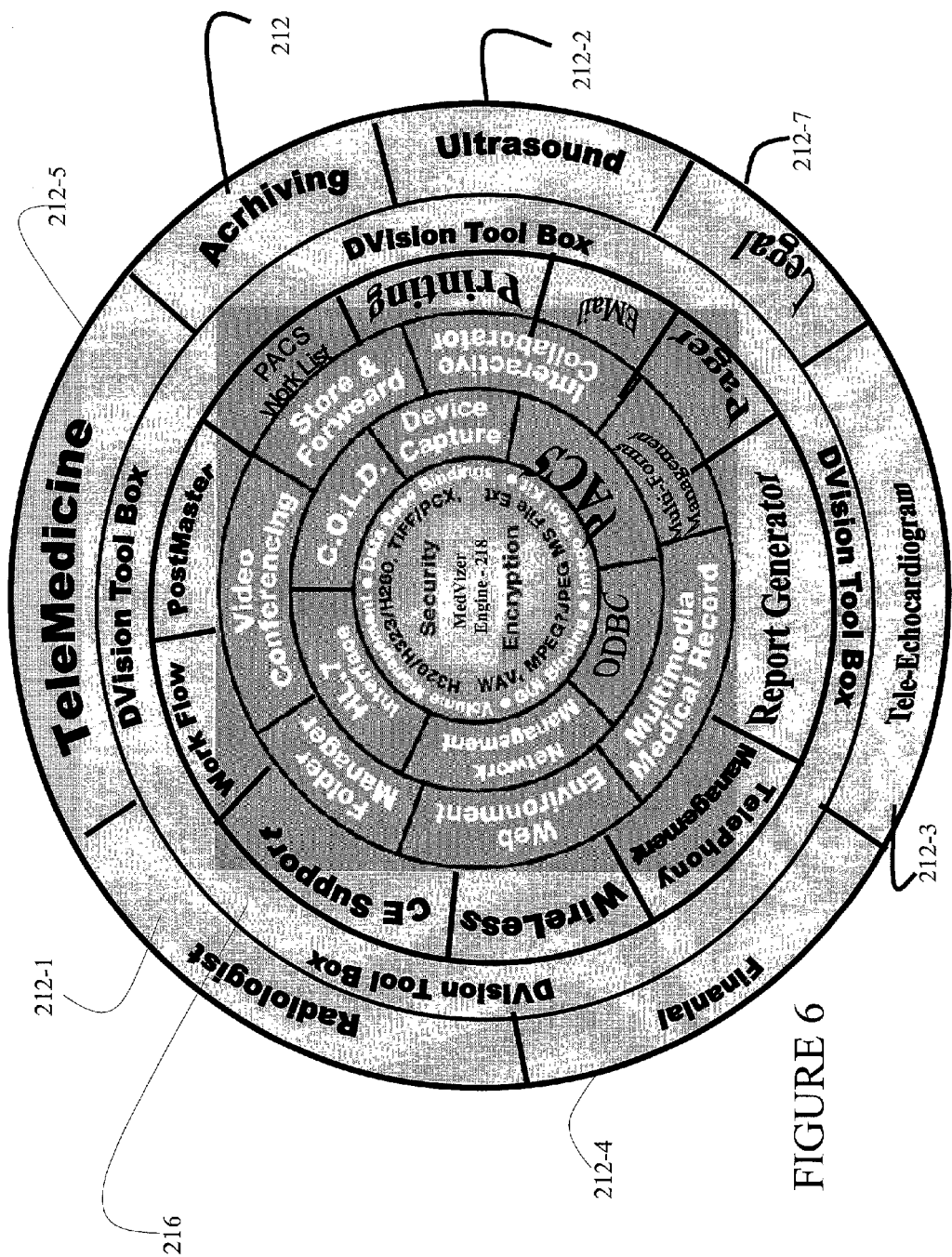
FIG. 6 shows a relationship between application software, the master control file, and the engine of the present invention.

FIG. 6 is a diagram of functions provided by engine 218, the master control file 216, and customer applications 212 such as radiologist 212-1, ultrasound 212-2, tele-echocardiogram 212-3, financial 212-4, telemedicine 212-5, archiving 212-6, and legal 212-7. More particularly, as shown in FIG. 6, the engine 218 provides the following functions:

Security encription;

WAV, MPEG/JPEG MS File extension, TIFF/PCX, H320/H323/H260;

GUI Binding, Image Tool Kit, Data base Bindings, Volume Management;

ODBC, PACS, Device Capture, C.O.L.D., HL.7 Interface, Folder Management, Network Management;

Multimedia Medical Record, Multi-Forms Management, Interactive Collaborator, Store & Forward, Video Conferencing, Folder Manager, Web Environment;

Report Generator, Pager, EMail, Printing, PACS Work List, PostMaster, Work Flow, CE Support, Wireless, Telephony Management.

Some of the technologies included in the portability enabling software 214, and more particularly, the engine 218, are:

Postmaster Server
MedVizer Desktop Manager
PACS Gateway/DICOM Manager
MedVizer.COM
Telephony Manager
Collaboration Manager (Camera/Device Control and Annotation Management)
Chat Manager
Computer Output to Laser Disk (C.O.L.D.)
Data Manager Services
Workflow Services
Folder Management
Report Generator
Image Manipulation Services
Enterprise Security Manager
Volume Management Services
Bar Code Services
Device Capture Manager
Video Conferencing
Interface Manager (HL7/DICOM 3.0)
Store & Forward Exchange Services
Multi-Form Management Services An overview of each of the foregoing the technologies included in the portability enabling software 214, and more particularly, in the engine 218, include:

Postmaster Server

The MedVizer Postmaster Server is an unattended message exchange and distribution facility that is designed to receive, manage, file, and distribute baskets of medical information. The Postmaster Server continuously monitors incoming message streams and automatically detects, isolates, and files secured patient medical record information. This approach enables a central filing system to addresses a critical version control problem associated with typical store and forward technologies. The MedVizer Postmaster is also capable of rerouting medical information to other secure and unsecured Internet mail facilities based on user-specified configurations.

The MedVizer Postmaster provides a secure Enterprise-wide mail infrastructure for all information managed by an institution, and provides a completely scalable offering, serving as few as one to as many as tens of thousands of users.

The MedVizer Postmaster includes the following key features:

Provides Enterprise-wide mail management and distribution features which integrate standard e-mail with secure patient medical record information Automatically files patient data in a MedVizer multimedia medical record Updates information in the medical Enterprise repository obtained via HL7 protocol transactions Files audio and video clips in their appropriate medical record designated area Alerts clinician/physician to incoming information Decrypts incoming patient information based on Public Key/secure certificate authentication technologies Supports POP3/IMAP message formats Audits receipt and distribution of all secured medical information The MedVizer Postmaster serves as the Enterprise Messaging Gateway, and can replace or be integrated with clients' existing organizational messaging environments. Most welcome in today's environment of increasing information overload, the MedVizer Postmaster can provide a fast and accurate exchange and distribution system of reporting of patient/physician interactions. In addition, it provides secured auditable receipt management and dissemination of transactions required to comply with mandates of HIPPA legislation.

MedVizer Desktop Manager

The MedVizer Desktop Manager enables ViTel Net's engineers to quickly craft elegant medical record management solutions for our MedVizer customers—doing so without programming and so avoiding delays in systems' operation. This allows our teams at ViTel Net to quickly and seamlessly integrate medical equipment, video and audio information sources as well as other information capture devices (such as digital cameras, scanners and badge readers). A complete medical record environment can be tailored in real time, incorporating forms management, image processing, video-conferencing, and data base integration. The entire set of ViTel Net technologies can be accessed through this Web-enabled and desktop application environment.

Key features include:

Facilitates seamless integration of information without the need for applications development Enables integration of legacy based system data with desktop-focused medical databases within the Enterprise Displays medical information in multimedia formats for comprehensive presentation and manipulation of the data Presents a unified desktop view of medical information, providing timely details about patient status Provides secure, device-independent access to medical information, using the Web, PDAs and standard desktop applications The MedVizer Desktop Manager provides a unique advantage for our customers: It can tailor the view of their organization's medical information as they wish to see it displayed on their PC screens. In addition, the data in the MedVizer Desk Manager is totally secured; and information access is provided only on an authentication basis.

PACS Gateway/DICOM Manager

MedVizer has implemented a state-of-the-art Picture Archive and Communication (PACS) Gateway which integrates high-resolution legacy radiographic information with MedVizer's Enterprise-wide information repository. The PACS Gateway provides a technology bridge between disparate technologies using DICOM 3.0 Push/Pull commands. This mechanism facilitates continuous monitoring of the information exchange and can alert clinicians/physicians to the availability of exchanged information. A complete audit trail of all information transactions is also maintained.

Key features include:

Integrates high-resolution radiography with ultrasound, echocardiology, MRI and CT imaging, and nuclear medicine modalities in a seamless information exchange environment Provides Push/Pull technology between disparate vendors' proprietary solutions, thus allowing our customers to leverage their existing technology investment Integrates RIS data with the imaging multimedia capabilities of the PACS Gateway, thereby providing seamless management, distribution and archiving of radiographic information Using DICOM 3.0 and HL7 protocols, the PACS Gateway achieves a unintrusive solution for making radiographic information an Enterprise-wide asset rather than a departmental data storage facility.

MedVizer's PACS Gateway enables the implementation of an Enterprise-level solution by leveraging existing legacy technologies to meet the challenges of accessing and disseminating radiographic information across the clinical care delivery setting.

MedVizer.COM

MedVizer.com extends MedVizer customers' reach on the Web via their own desktops. Users can gain access to the same look and feel of databases' content that are currently available in an institutional setting, any time and anywhere, by using the MedVizer.COM secure component of the Internet as a transport mechanism. The entire MedVizer desktop and all of its rich features and functions are made accessible through a standard browser environment. Authenticated users then can view and also share medical information through ViTel Net's secure Enterprise information exchange.

MedVizer.COM also supports the presentation of clinical information on a standard hand-held PDA. The entire medical record, including image access and manipulation are made easily accessible in this wireless technology environment.

Key features include:

Facilitates Web browser-enabled presentation of standard MedVizer desktop applications Provides PDA (personal digital assistant) accessibility to MedVizer's secure information environment Instantly transforms the dynamically built MedVizer desktop into Web enabled browser applications Supports complex imagery manipulation functions (image windowing/leveling, panning, zooming and rotation, distance measurement)

Provides secure encryption/decryption services to support HIPPA data processing requirements MedVizer.COM enables ViTel Net to deliver a single desktop environment to meet all of the internal as well as external needs of our customers. A single set of training materials can enable all users to understand how to be immediately effective in our secure medical record environment any time and in any place.

Telephony Manager

MedVizer's Telephony Manager maintains an address book for all users and organizations that have been granted access to the institution's secure Point-to-Point, LAN/WAN or dial-up Enterprise environment. The Telephony Manager exchanges address information with other MedVizer Telephony Managers using a TCP/IP protocol. Users can access all facilities through a single, unified address book provided with this MedVizer management mechanism.

The Telephony Manager provides the networking bridge to transcend all TCP/IP networking environments. MedVizer supports Microsoft Networks, Novell, Banyan, 3Com and Vax DecNet network operating systems.

Key features include:

Standardizes address books across vendor-specific applications

Secures information sharing and authentication between and among other MedVizer-enabled sites Supports connections using ISDN, LAN/WAN and dial-up networking protocols Supports most network operating systems that are deployed in hospital settings today MedVizer's Telephony Manager streamlines the management and administration of access to external connections to the Enterprise infrastructure. Users have a single address book even though the individual applications which comprise the Enterprise need and maintain their own address books independently.

Collaboration Manager (Camera/Device Control and Annotation Management)

MedVizer has integrated a remote camera control and device selection manager into their Enterprise solution offering. Users at the far end of a videoconference connection can control the local movement of a camera and the selection of the input device being used as a part of the clinical delivery process. In addition, users can interactively and remotely annotate the clinical information while participating in the videoconference. All of these capabilities can bring emphasis and focus to the collaborative process.

Key features include:

Facilitates remote camera selection and control (zoom and pan)

Allows remote source selection (digital cameras, video medical devices and support cameras)

Enables bi-directional live video annotation so as to enhance collaborative focus and minimize ambiguity MedVizer's Collaboration Managers allow videoconference participants to manage the acquisition and capture of clinical information more expansively even at a remote site. This facility enables the clinicians to concentrate on the care delivery process rather than on the technology used in the consultative care delivery process.

Chat Manager

The MedVizer Chat Manager contains a series of tools for supporting and enhancing the interactive consultative care delivery process—including both text and audio chat. Text chat provides a secure, interactive instant messenger information exchange. Using this tool, clinicians can share discreet medical information with patients and patients' family members while consulting in a live care delivery setting. The Audio Chat capability of Chat Manager augments the Enterprise care delivery exchange still further. It provides the capability to receive and store interactive voice conversations in the care delivery setting.

Key features include:

Facilitates interactive text information exchange in an secure, instant messenger environment Allows for conversational audio transmission while in a clinical information-sharing mode Provides capability for storing and retrieving audio conversations as an adjunctive annotation to the care delivery process The Chat Manager further extends the MedVizer Enterprise-wide delivery solution by providing a secure implementation of off-the-shelf technologies which extend the consultative care delivery process in the interactive exchange of care delivery information.

Computer Output to Laser Disk (C.O.L.D.)

MedVizer is uniquely equipped with Computer Output to Laser Disk (COLD) technology. This component of our Enterprise product offering integrates sophisticated forms management, data base management and image scanning capabilities into a powerful display and output facility. Current hard copy forms can be scanned and used as background wallpaper on which database information can be displayed or outputted to a printer. Fields can be defined on the background image and linked to databases within the users' organization. This capability maintains the current look and feel of the organization's existing workflow and information dissemination processes while enabling the organization to migrate information display and data access management to a state-of-the-art technology.

Key features include:

Integrates hardcopy forms scanned with MedVizer's MultiForm Manager

Breathes life into existing forms by linking images to information management facilities Maintains current form workflow while migrating the informational content to a state-of-the-art enterprise information repository Extends the look and feel of the Enterprise to the physical forms management environment A key advantage of the COLD technology in time-pressed institutions is its capability for immediately deploying existing forms into a migration strategy for information modernization. Current workflow activities can be maintained as the enterprise information repository is developed and made available to the entire institution. Furthermore, this facility extends well beyond the forms arena. Existing computer screens can be saved as scanned images and implemented as a COLD application, thereby providing a migration path to the organization's overall IT modernization effort as well.

Data Manager Services

MedVizer's Data Manager Services product offering is a multidimensional relational data base engine through which information is seamlessly managed across the enterprise in one or more database servers. This service can scale to a near-limitless number of simultaneous database connections, with real-time access performance capabilities. The Data Manager Services facility goes well beyond the standard database management environment by providing a means of linking information from both legacy systems and MedVizer specific information into a single Enterprise-wide data warehouse.

MedVizer's Data Manager Services extends the limits of current data base and file management technology with a patent pending data and volume management enterprise-wide approach. The Data Manager Services component of MedVizer operates in cooperation with our Volume Management Services, and provide a unique means of effortlessly managing extremely high volumes of multimedia information. Our approach to information management virtually eliminates the backup problems that are encountered with most other information management strategies. Data can be easily partitioned and managed across the Enterprise and integrated via Data Manager's indexing services to provide near instantaneous access to information.

Key features include:

Provides database binding which links information contained in legacy data base management applications with ViTel Net's Enterprise data repository Contains a powerful and flexible data field definition facility, which includes the following field types:
Look-up tables elements
Numeric, Text, and Date categories
Visible/Invisible Field Types
Constants Enables each data field that is maintained in the MedVizer Data Manager Services to be supported by a field-level index, thus improving the speed of access to the data Provides a unique means of handling multimedia information management when coupled with ViTel Net's Volume Management Services Has the potential for near-infinite growth for managing enterprisewide information assets The complexity of managing high volume multimedia information is eliminated by the ViTel NetEnterprise information management approach that is provided by Data Manager Services technologies. Data are seamlessly integrated across the Enterprise. Information is pulled and pushed to and from legacy systems via MedVizer's Data Manager Services. A genuinely unified view of all informational assets that is required by the institution is realized through use of this technology.

Workflow Services

The Workflow Services module of ViTel Net's Enterprise solution tracks the movement of information through each step of the business process. Patient record transactions can be monitored as they pass through each step of the institution's care delivery process. Tracking of each patient record transaction (such as lab test, or radiologic image or ultrasound video) can be aggregated at an organization level or monitored on an as-received basis by each individual clinician/physician who works within the organization.

Individually based privilege access to the records, as defined by each institution, can restrict a user's access to transactional-level monitoring. Each item that is moved within the business process as well as the individuals reviewing the information are audited in a clinical transaction-tracing log that is maintained by the Workflow Services module. In addition, our information tracking mechanisms meet or exceed HIPPA-regulated information control/access requirements.

Key features include:

Provides a full medical record-level element tracking facility

Facilitates complete clinical information flow, monitoring, and alerting

Enables both group- and individual-level information tracking capability

Contains a full-featured alerting facility to notify receiver of the receipt of requested information Transactional-level information is the lifeblood of the care delivery process. Information required for diagnosis and treatment, when moved efficiently within the organization, can significantly improve the care delivery process. ViTel Net's Workflow Service module's ability to track and alert users of the receipt of key information will substantially enhance the care given to patients by providing clinicians with timely and comprehensive information at their fingertips. Furthermore, an ability to track transactional information throughout the organization will reduce the overall liability of the institution.

Folder Management

MedVizer supports a case-level information aggregation paradigm. Information about a single episode of care or a series of visits which represent a single episode can be maintained in logical folders using ViTel Net's Folder Management technology. Information on demographics, clinically collected data, lab results, as well as images and videos is aggregated into a single view using our Enterprise information management and presentation environment.

Key features include:

Has the capability to manage clinical information by episode

Aggregates patient visit information and information collected during these visits in a single patient folder Allows information to be accessed within or across a set of folders, based on the users' access privileges Maintains demographic information that can be independent of the patient episode and can be integrated with the main institution's information system Case management is of critical importance in the care delivery process. ViTel Net's Folder Management technology decreases the burden on the institution by aggregating information based on related episodes of care. When MedVizer's Folder Management technology is employed, care delivery protocols can be engineered to coincide seamlessly with case management service needs.

Report Generator

The MedVizer Report Generator is a powerful script-like reporting tool, which can allow reports to be reviewed, printed, e-mailed, or faxed in a secure health care setting. The Report Generator allows the user to manipulate, format and aggregate information contained in or linked to the MedVizer Enterprise repository in order to meet the reporting needs of the institution. Complex multimedia reports can be generated and distributed quickly and seamlessly in support of the care delivery process.

Key features include:

Provides a powerful data access and manipulation scripting tool

Facilitates complex multimedia report generation capabilities

Supports fax, e-mail, display screen, or printed output

Enables aggregated or itemized information reporting

Summaries and extracted information from the delivery of clinical protocols must be supported in a flexible, efficient and user-friendly manner. Complex queries and reporting requirements can be easily satisfied by our Report Generator's varied capabilities. Using this timely reporting tools, outcome reports, detailed patient summaries or consult request reports can be defined and used at an institutional level.

Image Manipulation Services

ViTel Net has integrated a full-featured PACS image processing and manipulation capability into our MedVizer Image Manipulation Services product offering. The Image Manipulation Services can operate using DICOM 3.0, JPEG, TIFF, GIFF or PICX images. This capability can be operated in a LAN/WAN setting or executed across the Internet using only a Web browser and assumed user access to information privileges. Image Manipulation Services can also be accessed via a PDA.

Key features include:

Provides zoom and panning features (mouse-level zoom along with rectangular and ellipse magnification tools)

Facilitates image enhancements such as:
  Window additions and leveling
  Convolving (sharp, normal and smooth)
  Rotation, mirror and flip)

Enables annotation via
  Measurement lines
  Measurement areas
  Measurement angles Allows for CINE loop and auto loop Provides voice, text and graphic annotation capabilities Digital manipulation of easily accessed clinical information—available at any time and any place—is the cornerstone of MedVizer's Image Manipulation Services. Information visualization is significantly enhanced and training reduced when the same tool is used to process high-resolution color and radiologic images as well as low resolution faxes. Voice, text and graphic annotations can be stored and distributed with the images containing highlights of key findings or noted consultation requests.

Enterprise Security Manager

MedVizer maintains a secure shield around information and application access through our Enterprise Security Manager product offering. All access to information and application is controlled at a minimum by a password-privilege access model. A Public/Private Key (PK) can be supplied to further improve the authentication process and restrict access to our Enterprise environment. All data that are transferred outside of the Enterprise can be encrypted, based on user information-sharing preferences. All data movement or manipulation in the Enterprise is logged and maintained in an audit files database. HIPPA-compliant access restriction and a logging model have been incorporated into the Enterprise Security Manager.

Key features include:
Provides a password-privilege access model
Supplies PK certification and encryption/decryption
Generates a complete audit trail of all data manipulation activity Protecting patient confidentiality is critical to every health care institution today. Ensuring that only those people with a need to know sensitive patient record information will have access to it is the cornerstone of our product offering. ViTel Net has implemented a secure Enterprise-wide clinical delivery system of which the Enterprise Security Manager is a critical component. Using it, all information access is based on the institution's access-privilege model and is audited to ensure privacy and accountability has been strictly maintained.

Volume Management Services

The Volume Management Services component of our MedVizer wide ranging product offerings manages the storage and automated file-naming mechanism for all data sources that are incorporated into the patient's electronic medical record. Our technology integrates distributed information management services with logical volume management and stores the resulting file names and logical drive names in our Data Manager Service module. The Volume Management Services product is capable of handling any sized file quickly and efficiently. For example, very large multimedia files (measuring 200-500 Mb in size for echocardiology video studies) are managed and stored seamlessly in our electronic patient record.

T Volume Management Services solution uniquely supports fast reaction backup and an equally expedient recovery strategy for files that are managed in the enterprise environment. Files can be archived on either fixed or removable media, based on customer preference.

Key features include:
Provides distributed file management services that are capable of managing all files either on a single server or seamlessly across multiple database servers simultaneously
Enables improved backup/recovery based on a distributed file management strategy
Ensures a near-limitless information management capability using our distributed enterprise storage model ViTel Net's Volume and Data Manager services are uniquely capable of storing large volumes of medical video clips and large CINE Loops files on a single server for small heath care institutions or in a distributed multi-server environment for a large enterprise-wide solution. ViTel Net's Volume Manager is totally scaleable—from a single department-level server to a complete enterprise-wide solution

Bar Code Services

MedVizer's Bar Code Services reads and automatically files bar-coded scanned information or physical assets containing patient-related bar-coded information that is to be managed or linked to the patient's electronic medical record. Duplicate items will be flagged. The Bar Code Services product can also be used to update or replace existing information in an organization's radical databases.

Key features include:
Enables automated filing of patient-related information based on bar-code technology
Facilitates conflict management and resolution strategy for pre-existing information assets ViTel Net's Bar Code Services provides a bridge between the physical world of asset management and the logical information management required to support most enterprise-wide solutions. Using the Bar Code Services product, information is seamlessly filed and managed in a single electronic patient medical record. All such information is then made accessible anywhere within the enterprise, based on the institution's access privilege conditions.

Device Capture Manager

The MedVizer Device Capture Manager easily integrates all TWAIN-compliant imaging devices (digital cameras, scanner and video tape cameras) with other MedVizer data storage facilities. Information captured from imaging devices are automatically filed in the patient's electronic medical record.

Serial and wireless sensors are also supported through ViTel Net's Device Capture Manager. Reports related to patients' physiological measurements, such as pulse, blood pressure, temperature, breath flow measurements and blood sugar levels are but a few of the types of data that are possible to be captured by the Device Capture Manager. All information that is captured is automatically linked and stored in the patient's medical record.

Key features include:
Allows software control of device source selection
Supports plug-and-play video devices, cameras or SCSI page scanners
Provides automated filing assistance for information captured and sent via the Web or through a dial-up connection ViTel Net's Device Capture Manager makes it easy to connect foreign devices which utilize a TWAIN interface and to store the collected information directly in the patient's electronic medical record. MedVizer's VNet desktop can be easily configured to provide soft labels to access these foreign devices from the clinicians' desktop or that are captured remotely in a videoconference encounter.

Video Conferencing

MedVizer has seamlessly integrated a number of PC-based Video Conferencing applications into the MedVizer product enterprise environment. MedVizer's video conferencing facility is closely coupled to the video encoder and image capture card to provide our customers the ability to capture streaming video and still information in real time.

Key features include:
Supports H-260/262, H-320, and H323 LAN/WAN standards
Enables direct video and still-image capture
Captures entire video conference sessions and stores them in the patient's electronic medial record
Supports distance learning and physical consults in a shared information environment
Supports point-to-point and multi-point connections Video Conferencing enables the clinician/physician to consult with another doctor or review a patient's current status remotely. Information can be processed in real time for capture and asynchronous transmission to the health care institution. MedVizer seamlessly integrates this videoconferencing technology, thereby fully eliminating the need for special training to operate and maintain the equipment.

Interface Manager (HL7/DICOM 3.0)

MedVizer supports all HL7 and DICOM 3.0 transactions within their product offerings; and through the use of ViTel Net's Interface Manager, an organization's information can be seamlessly integrated into existing institutional informational systems using a push/pull transaction paradigm. The Interface Manager quickly integrates information from the organization's various labs, departments and hospital information systems.

Key features include:

Provides fully HL7 compliant tools for integrating information from legacy institutional systems Extracts and forwards fully DICOM 3.0-compliant radiology and cardiology information to and from existing department-level systems Integrates Lab Information (LIS) and Radiology Information Systems (RIS) into the electronic medial record ViTel Net's Interface Manager leverages the information content and management of legacy systems by seamlessly integrating this information across the enterprise using the MedVizer Interface Manager product offering.

Store & Forward Exchange Services

The MedVizer Store & Forward Exchange Services product offering contains a secure point-to-point medical record information sharing facility and a POP3-enabled e-mail distribution capability. All information is protected through a privacy key and can be encrypted to further restrict access to sensitive medical record information. The entire medical record or any subset of this material can be made easily shared. Sites currently equipped with ViTel Net's MedVizer software will automatically file patient data into an existing patient records or create new patient records once user access has been granted. Clients who are not yet using our software are forwarded the viewing mechanisms that are necessary to open and review the contents of the medical record once a standard user authentication process has been completed.

Key features include:

Provides full or partial medical record dissemination (depending on users' access privileges)

Supports point-to-point and POP3 distribution facilities

Ensures secured information packaging to prevent unauthorized access to sensitive medial information Provides automatic patient record filing and clinician/physician alerting for incoming information MedVizer program engines support asynchronous clinical consults using the Store and Forward Exchange Services product offering. Information can be reviewed, evaluated and recommendations can be returned in either an email or point-to-point communications environments. Security is critical to our approach and only holders of decryption keys will be granted access to this sensitive information on a need-to-know basis.

Multi-Form Management Services

MedVizer's Multi-Form Management Services product offering integrates desktop forms with the full range of services in the MedVizer database repository. Information can be organized in a seamless manner into customized forms that link an organization's and its patients' data from disparate information sources. These data can automatically be transferred to forms in a hierarchical manner, thus eliminating the need for data entry or information confusion. Logical data units such as patient, demographic, scheduling, billing or care delivery findings can be quickly implemented and presented to the user in an organized, efficient manner.

Key features include:

Supports database fields, look-up tables, sight constants computational fields, visible or invisible fields, and auto fill based on other field data entry Enables single or hierarchical form facility Provides capability for shared information across form hierarchies Transfers binding legacy fields from external databases to screen elements ViTel Net's Multi-Form Management Services is a powerful tool which allows ViTel Net's engineers to quickly create user-friendly information environments for our customers. Forms are created without the need for programming and are totally Web enabled once the definition process is completed.

Figure 7:
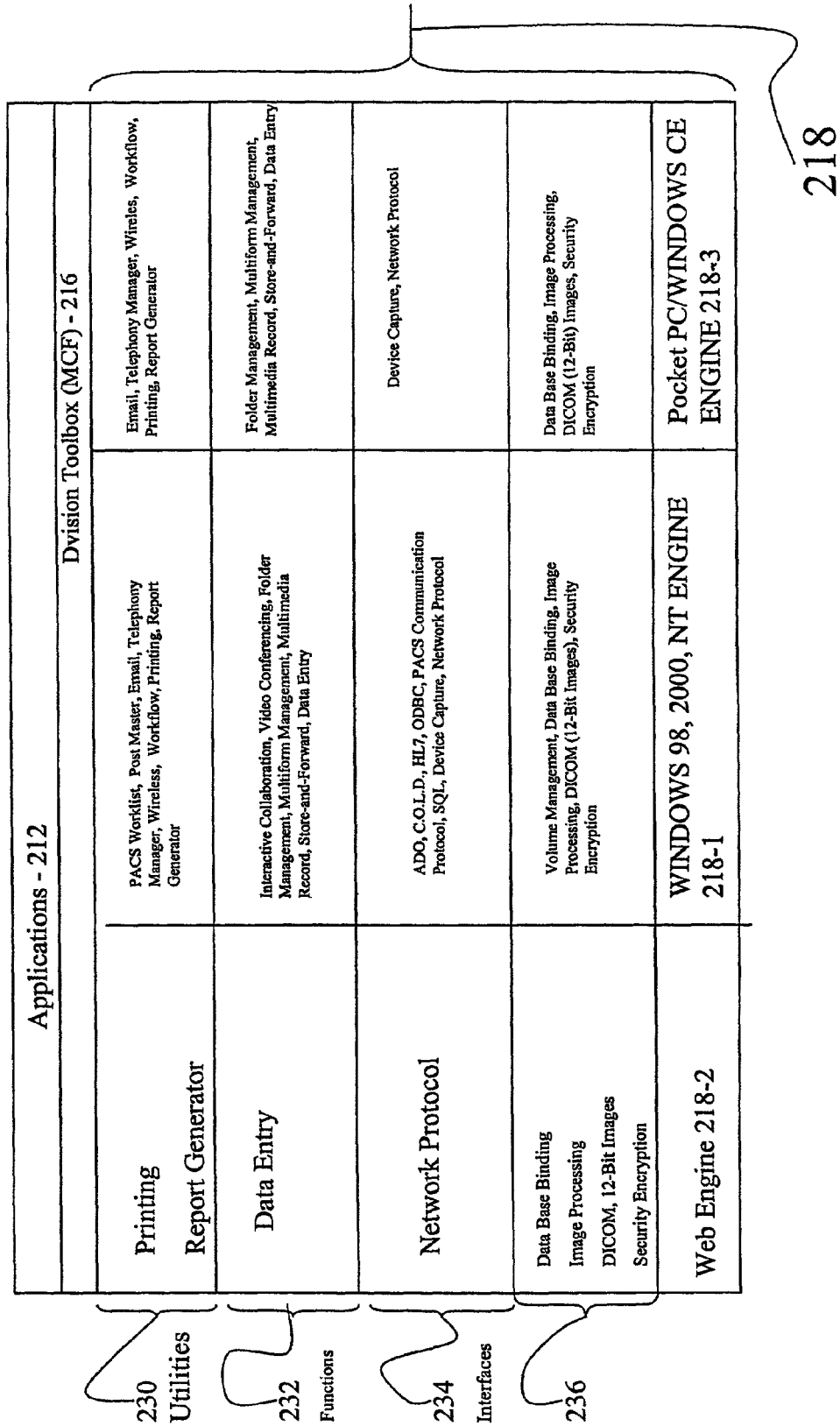
FIG. 7 shows application software, a master control file, and engines.

FIG. 7 is an overview of the relationship between the application software 212, the master control file (or Dvision Toolbox) 216 and the engines 218. The engines include WINDOWS 98, 2000, NT engine 218-1; Web engine 218-2; and POCKET PC/WINDOWS CE engine 218-3. The WINDOWS 98, 2000, NT engine 218-1 is known in the art. The Web engine 218-2 is an aspect of the present invention. The POCKET PC/WINDOWS CE engine 218-3 is another aspect of the present invention.

WINDOWS 98, 2000, and NT are operating systems typically executed by a personal computer. WINDOWS CE is an operating system executed by a pocket device.

As shown in FIG. 7, the applications 212 and the master control file 216 remain constant when ported between engines 218-1, 218-2, and 218-3. That is, the master control file 216 of the present invention, when read by any of engines 218-1, 218-2, or 218-3, allows the application software 212 to be executed by the engines 218-1, 218-2, or 218-3. The division toolbox 216, which includes the master control file 216 of the present invention, supports utilities 230 printing, and report generator for the web engine 218-2; PACS work list, postmaster, e-mail, pager, telephony manager, wireless, workflow, printing, and report generator for engine 218-1; and e-mail, pager, telephony manager, wireless, workflow, printing, and report generator for engine 218-3. Moreover, functions 232 include data entry supported for engine 218-2; interactive collaboration, video conferencing, folder management, multiform management, multimedia record, store-n-Forward and data entry for engine 218-1; and folder management, multiform management, multimedia record store-n-forward, and data entry for engine 218-3. Interfaces 234 include network protocol for web engine 218-2; ADO, C.O.L.D. HL7, ODBC, PACS Communication Protocol, SQL Device Capture, and Network Protocol for engine 218-1; and device capture, and network protocol for engine 218-3. Moreover, additional functionality 236 is supported such as data base binding, image processing, DICOM, 12-bit images, and security enkrypton for engine 218-2; volume management, data base binding, image processing, DICOM, 12-bit images, and security encryption for engine 218-1; and data base binding, image processing, DICOM, 12-bit images, and security encryption for engine 218-3.

Generally, the engines 218 include a set of programs, functionalities and interfaces designed for cross-platform operating systems. The engines 218 populate the database and provide the functionalities for the applications created with the Dvision Toolbox 216.

A key component in the engines 218 is the MedVizer Basket. The MedVizer Basket presents a new approach to the seamless integration of information in a healthcare enterprise on intranets or across public and private Internets. Patient episode data are captured, compressed, encrypted, and encapsulated into a single secure file. The MedVizer Basket allows complete medical records to be shared in a secure environment, regardless of the source of information origin. The MedVizer Basket can include information pulled from or pushed to an existing Hospital Information Systems (HIS), Radiology Information Systems (RIS), Picture Archive and Communication Systems (PACS) or Laboratory Information Systems (LIS) by using standard protocols such as HL7 and DICOM 3.0. Electronic Medical Records can also be shared external to the institution with the MedVizer Basket by using encrypted SMTP or POP mail messages.

The combination of the Dvision Toolbox 216 and the engines 218 enables the portability enabling software 214 of the present invention allows for rapid customization of cross-platform telemedicine/e-health applications in areas such as Radiology; Echocardiography; Ultrasound; ENT; Dermatology; Pathology, and General Medicine.

In an Enterprise-wide environment, the applications 212 when interfacing to the portability enabling software 214 of the present invention enable workflow that allows each patient record to be tracked from start to finish and provide customized operator interfaces that are targeted specifically for the individual phases in the workflow are created in a programmer-less environment and yield a complete solution.

Figure 8:
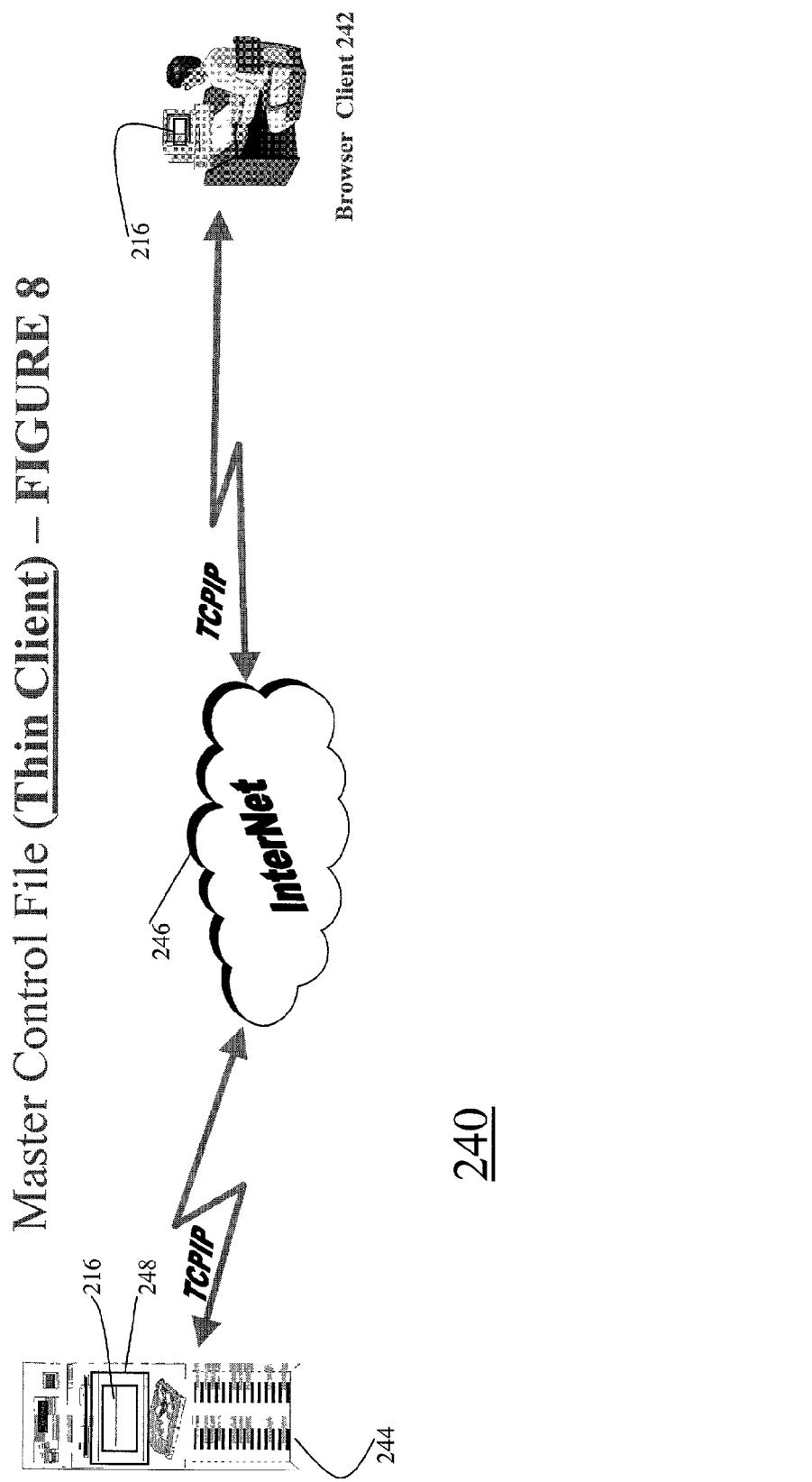
FIG. 8 shows a computer system of the present invention.

FIG. 8 shows a computer system 240 of the present invention in which the master control file 216 of the present invention is implemented. In the computer system 240 of the present invention, a browser client computer 242 accesses a web server 244 through a network 246. Network 246 comprises computer networks such as the Internet, an Intranet, an Extranet, and others. An example of a communications protocol which the browser client 242 may use to access the web server 244 over the network 246 comprises TCP/IP. However, other communications protocols may be used. Alternatively, the browser client 242 may access the web server 16 directly through telephone communications.

An example of a web server 244 includes a web server executing WINDOWS NT 4.0 with Exchange. The web server 244 comprises the master control file 216 of the present invention, as will be explained.

The web server 244 executes and stores computer program 248. The computer program 248 includes the application program 212 and the portability enabling software 214 of the present invention. The portability enabling software 214 of the present invention includes the master control file 216, the engine 218, and the support files 220. A part of the master control file 216 is stored on the server 244, and another part of the master control file 216 is stored on the client computer 242.

More generally, the program 248 includes control files such as the master control file 216, MNU, and folder image; support files such as DVDICOM.OCX, VITELNET-VIEWOCX.OCX, C4.DLL, CVIEW32.DLL; and additional programs including DEFAULT.ASP and PAGE1.ASP.

Figure 9:
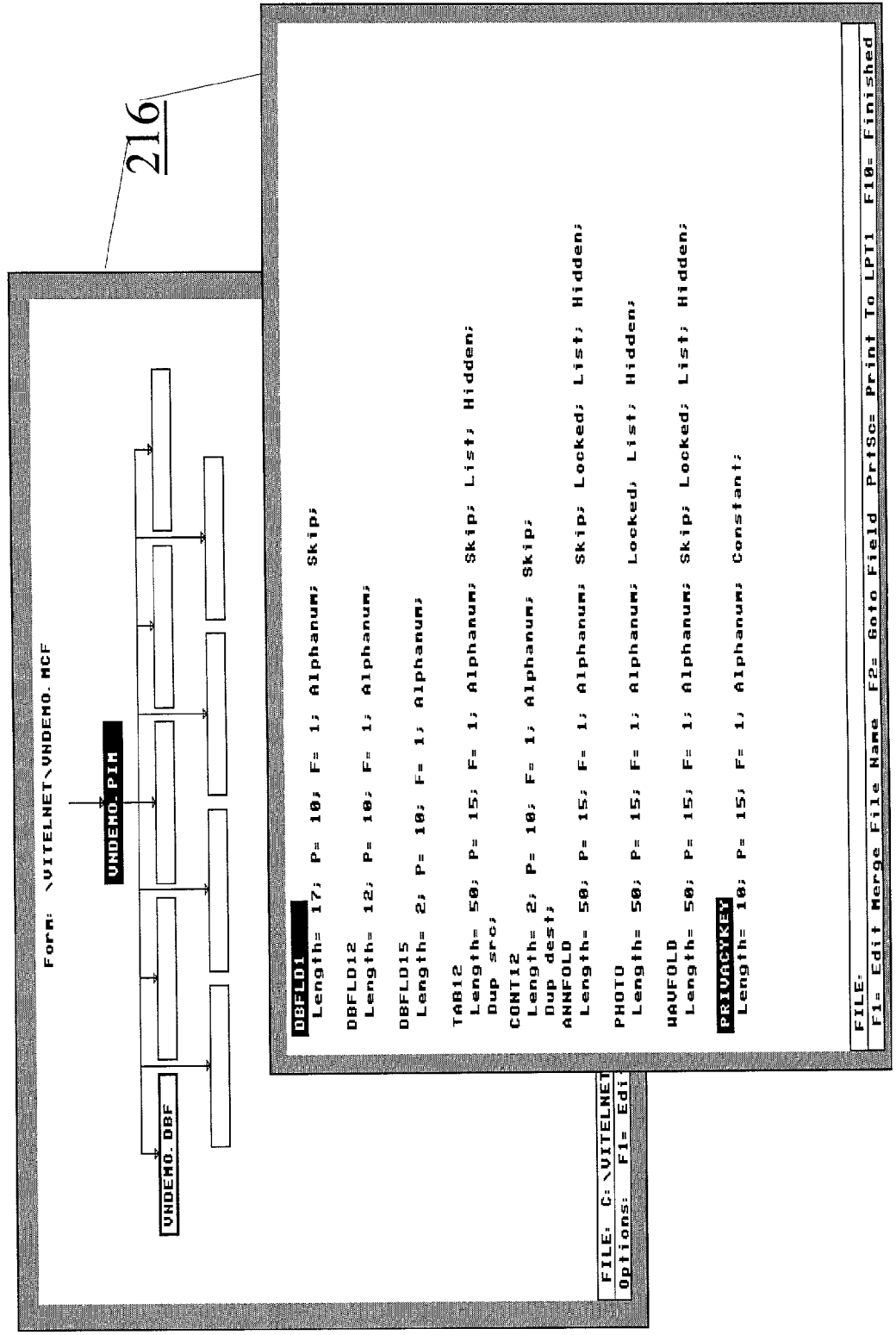
FIG. 9 shows a master control file included in the present invention.

FIG. 9 shows master control file 216 of the present invention. As shown in FIG. 9, master control file 216 of the present invention includes field names, lengths, and other information related to the field.

Figure 10:
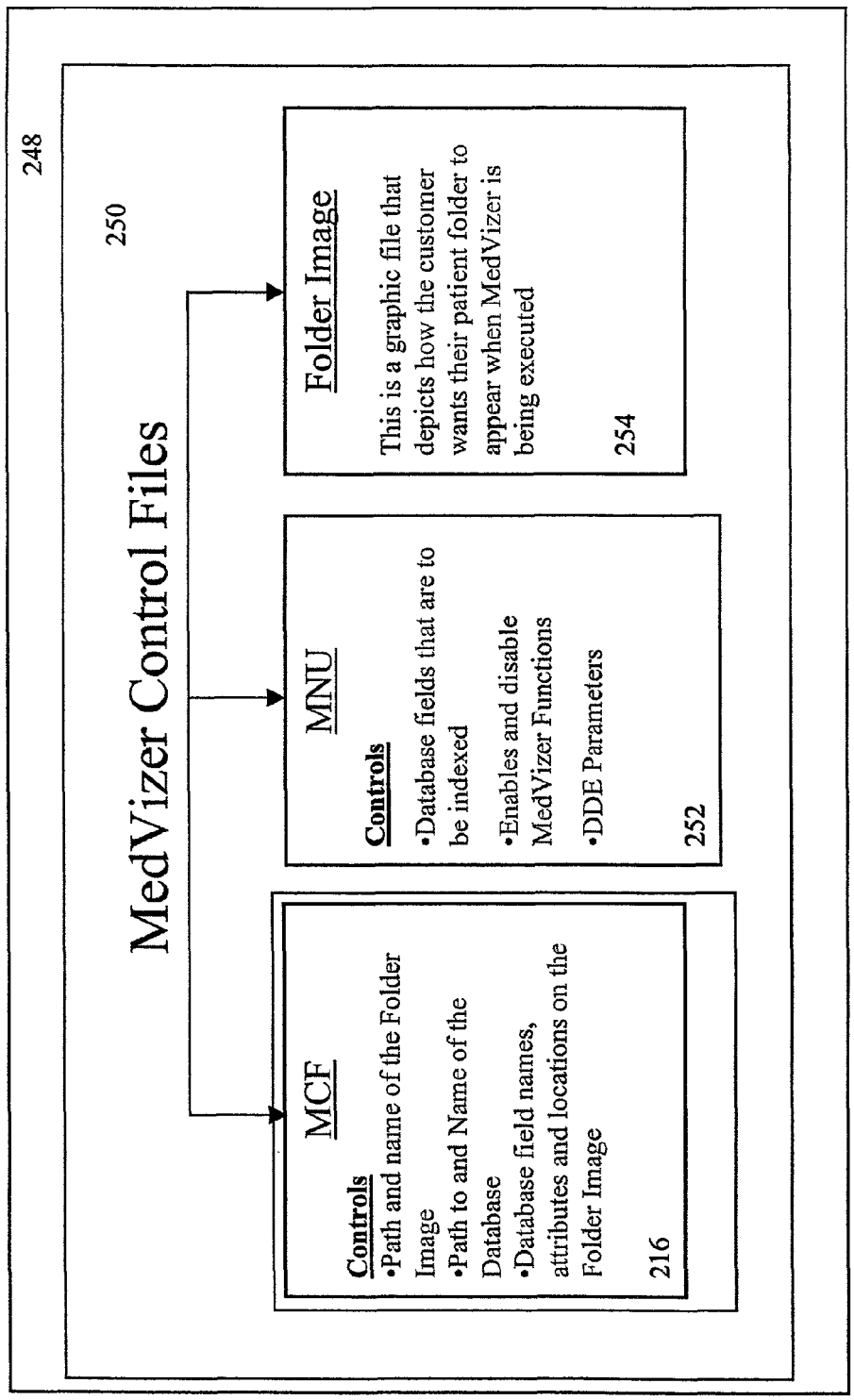
FIG. 10 shows MEDVIZER control files.

FIG. 10 shows the control file 250 included in program 248. As shown in FIG. 9, the master control file 216 controls the path and name of the folder image, the path to and the name of the data base, the data base field names, attributes, and locations on the folder image. The MNU 252 controls the data base fields that are to be indexed, enables and disables functions (such as MEDVIZER functions) and DDE parameters. The folder image 254 is a graphic file that depicts how the customer wants their patient folder to appear when an application program (such as MEDVIZER) is being executed. Each of the control files 250 is easily changed go customize the application program (such as MEDVIZER) to file the customer's needs without performing any programming.

FIG. 11A shows the DEFAULT.ASP 260, which is executed by the web server 244. As shown in FIG. 11A, the DEFAULT.ASP 260 file executed by web server 244, includes a program.

FIG. 11B shows the program PAGE1.ASP 262, included in the programs 244, but executed by Browser client 242. As shown in FIG. 11B, PAGE1.ASP 262 includes a program.

FIG. 12 shows a flow chart 500 of retrieving folder images stored on the web server 244. Retrieval of the folder images is initiated by the Browser client 242, in communication with the web server 244 through network 246.

Referring now to FIG. 12, the user keys in http://Vitelnet/ Vitelnet, as process 502.

The Browser client 242 then receives files and programs from the web server 244 in process 504. More particular, the Browser client 242 receives the master control file of the present invention 216 (entitled VitelNet MCF), the M522 file (entitled VitelNet.MNU), Vitelnet.DBF, DVDICOM.OCX, VitelnetViewOCX.OCX, C4.DLL, CVIEW32.DLL, CVIEW32.DLL, and DEFAULT PAGE 260, from the web server 244. In process 506, search criteria is submitted from a Browser client 242 to the web server 244. Next, in process 508, the Browser client receives the search list from the web server 244 with the DEFAULT PAGE. The user, using the Browser client 242, selects the patient from the DEFAULT PAGE search results list, in process 510. Then, the Browser client 242 receives PAGE1 262 program from the web server 244, in process 512. Subsequently, in process 514, the user uses the patient folder images on the Browser client 242.

FIG. 13 shows a series 620 of screens, which are displayed on the Browser client 242 upon execution of the process 500. Referring again to FIG. 12, search criteria is submitted in process 506 using screen 622. Then, a search list is received, in process 508, and displayed on screen 624. Once the patient is selected in process 510, the patient folder images are displayed, in process 514, on screen 626. Folder images shown in screen 626 include a photograph of the patient 628, and other medical images 630 which are included in the folder images corresponding to the selected patient.

Figure 14:
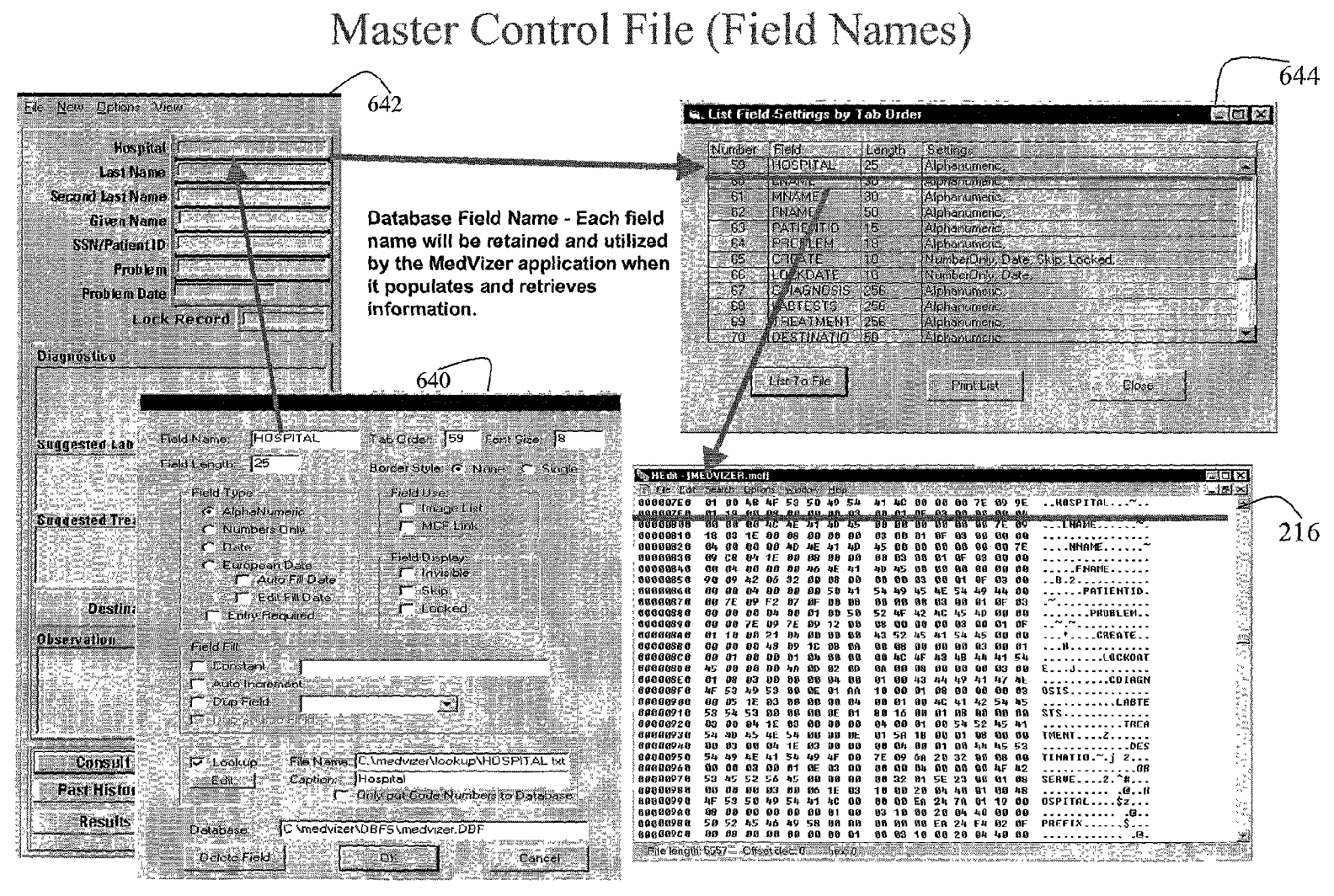

FIG. 14 shows establishment of field names in the master control file 216 of the present invention. As shown in FIG. 14, a data base definition screen 640 provides the user with the capability of defining a field name, a tab order, a font size, a field length, a border style, a field type, a name of a file in which the field may be looked up, a definition of the field, and the data base name. This field name, for example, hospital, is then shown on a user screen 642, and is also listed on a list field settings by tab order screen 644. In addition, the field name is stored in the master control file 216 of the present invention. The field name, which is a data base field name, is retained and utilized in the application software (such as MEDVIZER) when the application software populates and retrieves information.

Figure 15:
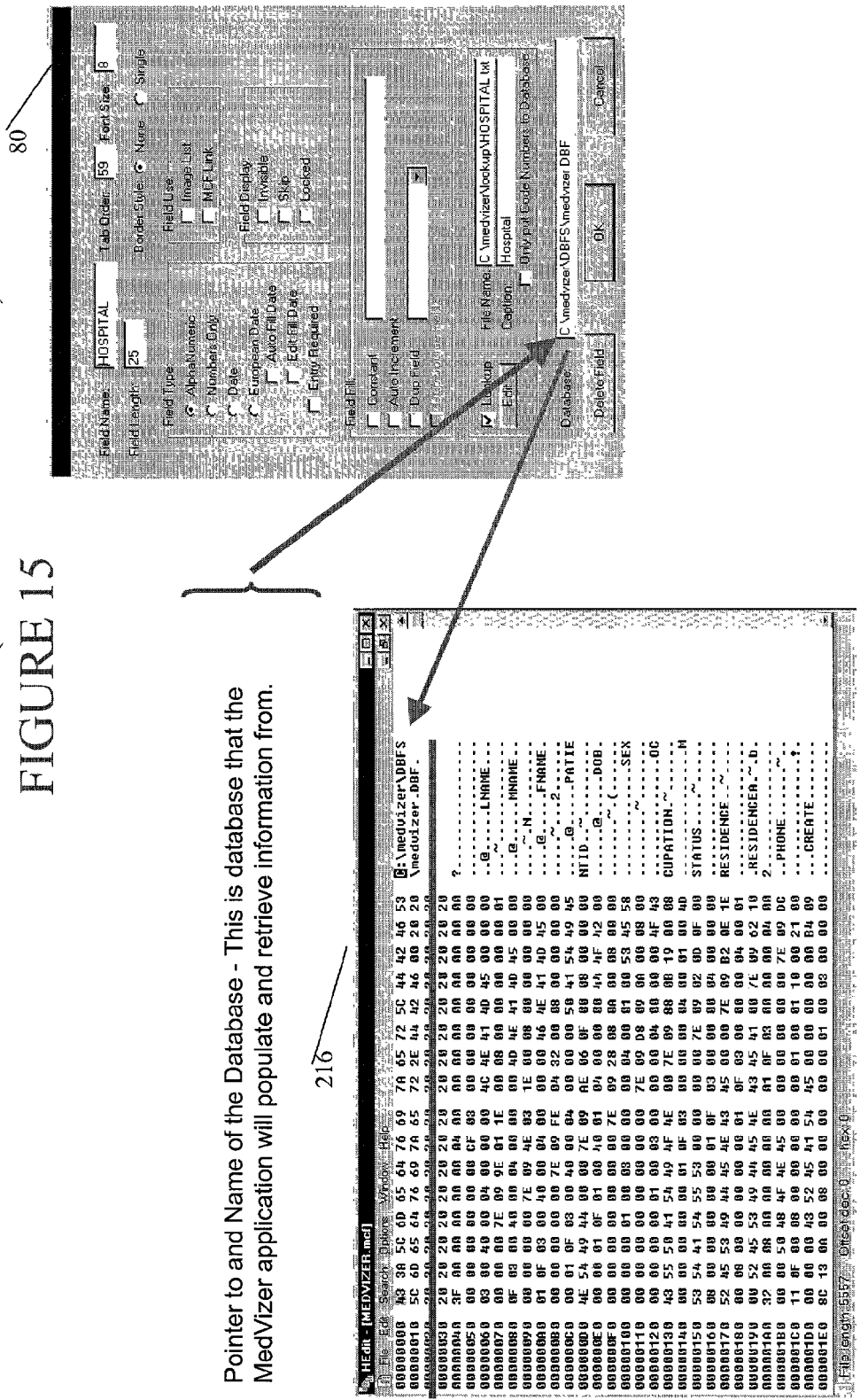
FIG. 15 shows master control file database pointer.

FIG. 15 shows a relationship between a data base pointer and the master control file 216 of the present invention. As shown in FIG. 15, a data base pointer to the data base that the application software (such as MEDVIZER) will populate and retrieve information from his established in the master control file 216 using screen 640.

Figure 16:
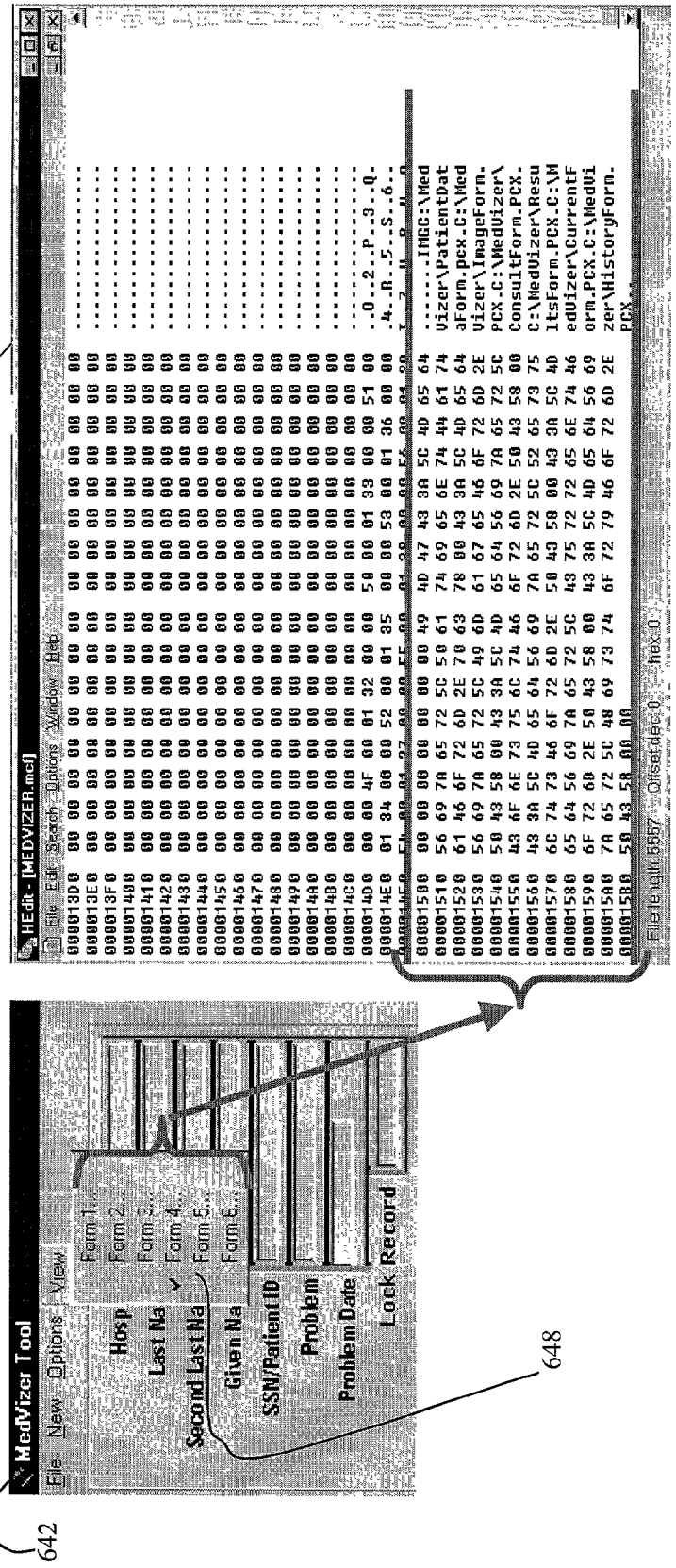
FIG. 16 shows master control file multiple forms.

FIG. 16 shows a relationship between a pointer 642 and name of graphic images that display when the application software (such as MEDVIZER) is executed, using an application software tool 648. The pointer to and name of the graphic images are stored in the master control file 216 of the present invention, as shown in FIG. 16.

FIG. 17 shows establishment of the master control file 216 field locations and attributes. As shown in FIG. 10, screen 640 allows to define information included in the master control file 216 of the present invention.

Figure 18:
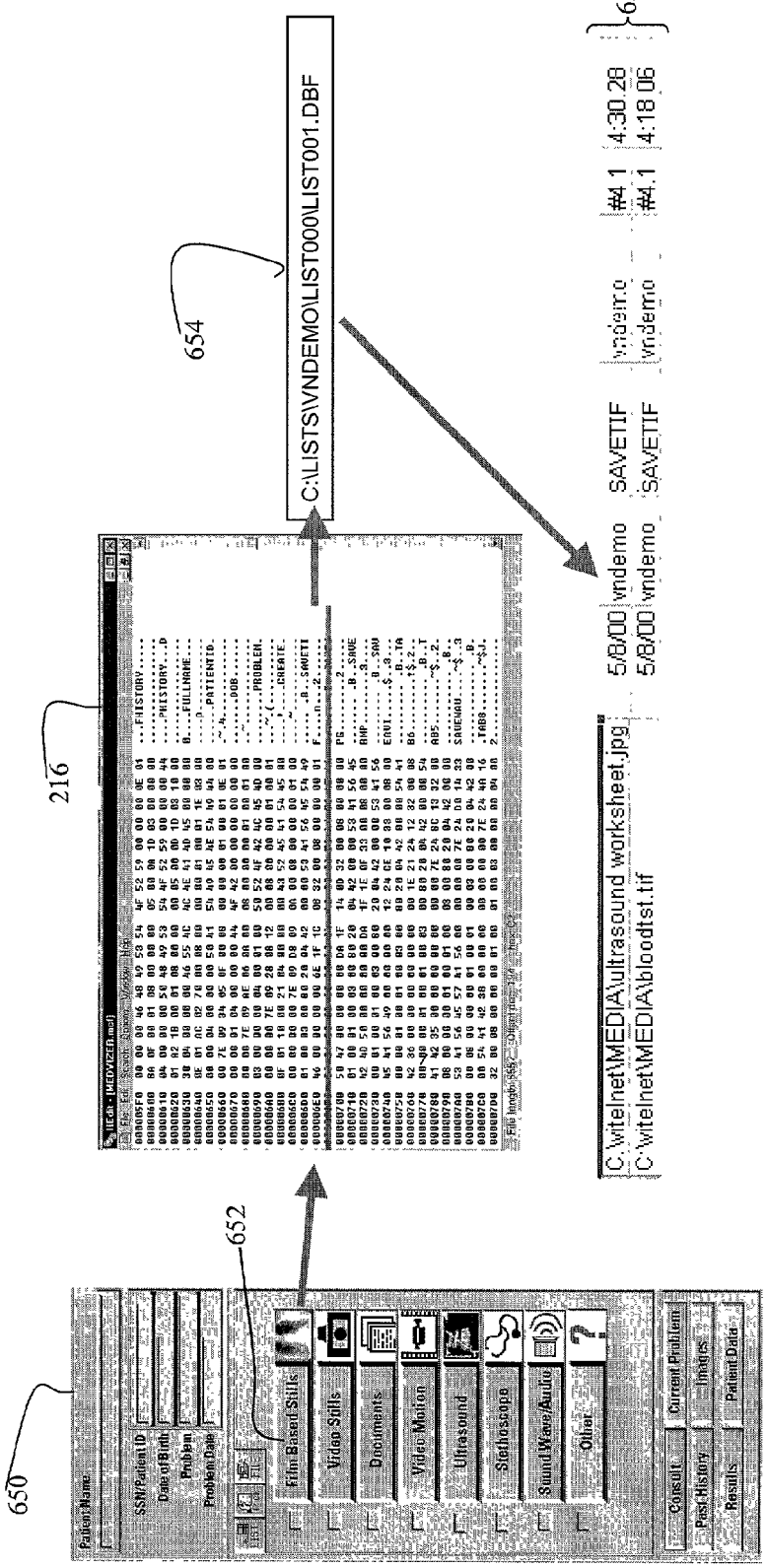
FIG. 18 shows MEDVIZER object storage and retrieval.

This information included in the master control file 216 of the present invention includes:
  Pointer to and Name of Graphic Image(s)—This is the image(s) that displays when the MEDVIZER application is executed.
  Pointer to and Name of the Database—This is database that the MEDVIZER application will populate and retrieve information from.
  Database Field Name—Each field name will be retained and utilized by the MEDVIZER application when it populates and retrieves information.
  Database Field Location—This is the top X Y coordinates that define the location that the database field will be displayed on the Graphic image when the MEDVIZER application is executed.
  Database field attributes
    Field Length
    Alpha/Num
    Numeric Only
    Date (North American/European Format)
      Auto filled with system date when database record is created.
      Auto fill when database record is modified.
      Fill from keyboard.
    Image List—Document Reference Point: List of archived documents maintained and displayed from this field
    MCF—Document Reference Point: Another mcf is accessed from this field; points to another MCF
    Invisible—Field data is not displayed
    Constant—Data is auto filled with a constant
    Skip—Field bypassed during data entry; prevents from anchoring on cursor field
    Required—Data must be entered into field
    Lock—Prevents user from entering/changing field content.
    Font—Defines font selection for this field
    Tab Order—Sets the tabbing order when Tab key is pressed FIG. 18 shows objects storage and retrieval using an image list field, with the master control file 216 of the present invention. As shown in FIG. 18, and image list 652 is selected from screen 650, which accesses the master control file 216 of the present invention. The master control file 216 of the present invention stores a pointer 654 to a data base which includes entries 656 of images, dates, and other information, for the corresponding patient name shown on screen 650.

FIG. 19 shows object storage retrieval using the pointer 654 to the data base name retrieved from the master control file 216 of the present invention. As shown in FIG. 19, the pointer 654 includes the name of a data base storing images 656. Objects supported includes DICOM (DC3, DCM, PIC), TIF, JPG, MPG, WAV, BMP, TXT, etc. . . 656-1. The pointer 654 is stored in the patient data base tab 658 of the master control file 216, and is referred to by the volume maintenance screen 660. The application software (such as MEDVIZER) locates the object using the pointer 654 that is in the patient folder data base 658. Object storage is determined the application software's volume management. Object naming and destination is automatically created in the control book. None of this requires any programming, and the volume and path is easily changed by the customer.

FIG. 20 shows a secure wireless telemedicine enterprise system 700 of the present invention. The system 700 includes a home client (on which part of the master control file 216 resides) which communicates via the Internet (using TCP/IP) 246 with a network (using CDMA (code division multiple access) at 128 KB) 702 and a PDA (personal digital assistant) 704. The PDA 704 includes the application architecture 200 of the present invention shown in FIG. 4. The PDA 704 is a wireless, mobile device and comprises a home monitoring system. Moreover, the home client 242 communicates with a hospital local area network (LAN) 706 (running at 100 MB, for example) through the Internet 246. The hospital LAN 706 interfaces to a hospital information system 16 (using HL7, SQL, ODBC, and ADO), a knowledge base WEB server 708, a WEB server 244, a server 710 (which includes a file server for a patient data base, a mail server with a rec. basket, and a postmaster with a process basket), and a wireless local area network (LAN) 712 (300'-2 MB/100'-11 MB). The wireless LAN 712 communicates with a hospital PDA (personal digital assistant) 714 which includes the application architecture 200 of the present invention.

FIG. 21 shows a telemedicine system 800 of the present invention. The system 800 includes a server 802 coupled to a local area network (LAN) 803. The LAN 803 is coupled to a radiologist system 804, which includes a computer, headset, scanner printer, monitor with camera, and monitor with working screen. The radiologist system 804 receives cases from the sonographer, views active cases, requests more scans (attach audio or text note), initiates audio calls (audio portion of video conferencing), initiates video calls (video conference audio and video), releases a patient, and views history.

The local area network 803 is also coupled to a wide area network (WAN) 806, which is coupled to the radiologist system 804 through TCP/IP, to a physician workstation 26 (using a DICOM/Pull with TCP/IP), an image acquisition station 22 (through a DICOM/Push. using TCP/IP), and a sonographer system 808. The sonographer system 808 includes an ultrasound machine, a computer, a monitor with a working screen, a headset, a monitor with a camera, and a scanner/printer. The sonographer system 808 is coupled to a wireless VC remote 810 implementing the architecture 200 of the present invention. The sonographer system 808 selects case from a schedule, adds patients that are not in the schedule, captures snapshots and video clips, scans paper documents, sends case data to the radiologist, views/plays text/audio notes, performs more scans, and releases the patient.

FIG. 22 shows a telemedicine system 900 in which VITEL NET application software 212 is implemented. As shown in FIG. 22, the system 900 includes a network backbone 902 interfacing to a wireless network 702, a sonographer station 808, a patient data base server 710, and a web server 244. The web server 244 interfaces to the Internet 246 then to a browser client 904 including the architecture 200 of the present invention, to transfer a patient folder 906 using TCP/IP. Moreover, the patient database server 710 interfaces through a small computer systems interface (SCSI) to RAID archive 910 to store and retrieve the patient folder 906. The patient database server 710 also interfaces through a TCP/IP dial-up to a fat client 911 implementing the architecture 200 of the present invention. The wireless network 702 interfaces to a PDA 704 implementing the architecture 200 of the present invention. The PDA 704 also interfaces wirelessly to the sonographer system 808.

FIG. 23 shows a communications architecture 1000, which includes application software 212, an operating system 223 (such as WINDOWS 98, WINDOWS 2000), and well-known communication protocols 1002 including HL-7, DICOM, H323, TCP/IP, and RS232. The HL-7 (health level 7) protocol is used to perform services such as populating the data base and scheduling patients. The DICOM protocol is used to perform services such as digital imaging and communication in medicine, including push, pull, get, move, and print. The H323 protocol is used to perform services including video conferencing, audio, video, and data communication. The TCP/IP protocol is used to perform services including application communications through ports, application #6367, camera #6368, video window #6369, phone #6365, MED-VIZER #6364, camera AMX #6362, and Streaming Audio #6370/6371. The RS232 serial port is used to perform services including data collection device interfacing, camera interfacing, and video sw box.

WINDOWS sockets interfacing is well-known in the art. FIG. 24 shows VNET/MEDVIZER connection flow 1100 using WINDOWS sockets. The connection flow 1100 includes a PDA 704 implementing the architecture 200 of the present invention to execute application software 212.

FIG. 25 shows remote TCP/IP function using the WINDOWS sockets discussed herein above.

FIG. 26 shows VNET/MEDVIZER 1210 software as distributed between VITEL NET application software 212, video capture, and MEDVIZER.

FIG. 27A and FIG. 27B show a VNET/MEDVIZER INI file 1300.

FIG. 28A and FIG. 28B show a MEDVIZER MNU file 252.

FIG. 29 shows a system start up group 1400, including establishing VITEL NET video conferencing properties 1402 and PHONE properties 1404.

FIG. 30 shows VNET properties 1500.

FIG. 31 shows the VNET desktop 1600.

FIG. 32 shows the MEDVIZER PHONE BOOK 1700.

FIG. 33 shows the volume information and generation 1800.

An aspect of the present invention comprises a master control file which makes formation of standards an open and continual process. The master control file of the present invention forms a self-sustained foundation for standardization of medical information systems. When computer system requirements change, the master control file of the present invention buffers computer system users from those changes so that the users can maintain their patient medical record information systems without changes.

In addition to the development of new protocols, the master control file of the present invention assists existing standards in working with one another. That is, the master control file of the present invention forces system developers to adhere to recommended standards and protocols and, therefore, any company participating in the area of medical information from development of medical devices to the insertion of information into an electronic patient record may do so confident that their systems will be compatible with other systems and components adhering to the recommended standards.

The master control file of the present invention is created by the MEDVIZER TOOLBOX and includes information that defines and provides the customer application with the interoperability to populate, maintain and retrieve information from its database.

Moreover, reference is made to the following definitions of terms:
ASP—Active Server Page
HTML—HyperText Markup Language
CGI—Common Gateway Interface
URL—Uniform Resource Locator
OCX—OLE Custom Control
ActiveX—OLE and OCX implementation under a new name.
TCP/IP—Transmission Control Protocol over Internet Protocol
HTTP—HyperText Transmission Protocol
DLL—Dynamic Link Libraries Another aspect of the present invention includes a pocket device (such as a Personal Digital Assistant, or PDA) executing a global medical records system. The pocket device executing a global medical records system is discussed in Provisional Application U.S. Ser. No. 60/221,558, filed Jul. 28, 2000, the contents of which are incorporated herein by reference.

The global medical records system corresponds to the architecture 200 shown in FIG. 4.

The Global Medical Records system of the present invention enables health care providers with the ability to remotely obtain to review the complete patient record or view key health indicators such as heart rate, blood pressure, blood-oxygen and blood-sugar levels by the use of Pocket Devices (PD).

Using the Global Medical Records System of the present invention, patient episode data is captured, compressed, encrypted, and encapsulated into a single secure file and e-mailed to the repository's mail server. MedVizer Postmaster, located on the repository's mail server, is continuously running and processing mail as it is received. The mail is de-encapsulating, uncompressing and the episode is automatically filed into the patient medical record. As the mail is processed a pager messages and/or email message is sent to the assigned physician notifying them of the receipt of patient episode data.

The Global Medical Records system of the present invention simplifies and organizes the collection of all patient data into a patient folder system. A patient medical record typically contains:
Patient demographic data;
Scanned (nursing notes, doctor's notes and many miscellaneous documents);
X-Ray (DICOM Files);
Images (Ultrasound, etc.);
Video (MPG)
Image Stills (JPG);
Sound and Audio annotation (WAV);
Word processing documents;
Information from the hospital (MIS); and
Vitals data (heart rate, blood pressure, blood-oxygen, etc.).

Using the pocket device global medical records system of the present invention, the physician can review outstanding cases, provide consultation as well as accessing the entire patient database from their home or office. During the viewing process the following functions are available:
Graphically display Vitals (Visual evaluation with respect to the patient's clinical and historical picture);
Zoom and Pan features (mouse level zoom along with rectangular and ellipse magnification tools);
Window and Leveling;
Histogram;
Data Elements (DICOM);
Convolve (Sharp, Normal and Smooth);

Measurement (Line, Area, Angle); and

Image manipulation tools (rotation, mirror and flip).

Figure 34A:
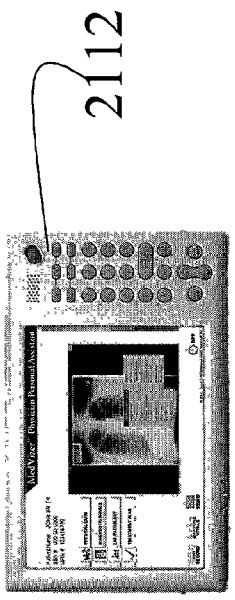
FIG. 34A, FIG. 34B, and FIG. 34C show pocket devices.
Figure 34B:
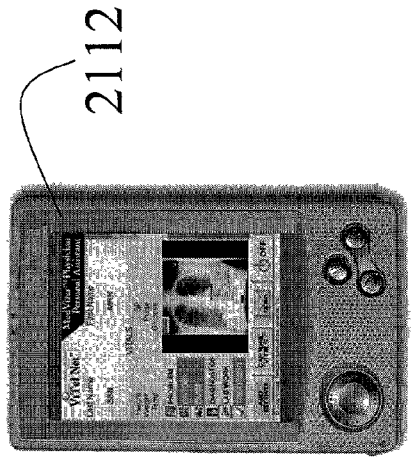
Figure 34C:
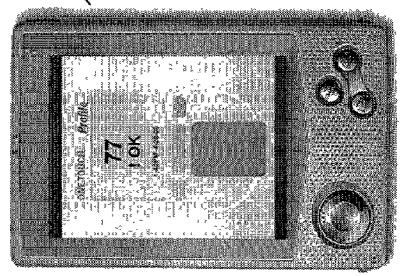

FIG. 34A, FIG. 34B, and FIG. 34C show examples of a pocket device 2112 of the present invention which provides physicians with the ability to view patient records including medical images (DICOM 3.0 compliant) via e-mail, anytime and anywhere.

The Pocket Device of the present invention acquisition is a home care monitoring solution that automatically captures, compresses, encrypts, and encapsulates patient episode data into a single secure file and sends patient data via Internet e-mail to the referring facility for review eliminating scheduling office visits and the time to travel for those visits with this one-touch capture and sending device.

Features of the Pocket Device of the present invention include:

Pocket Device, MFG Cost Less Than $700, with Color Colors 65550;

640×480 resolution;

Touch screen;

Fit in the palm of your hand;

Mobile;

Light Weight;

Easy to Use;

Durable;

Cordless battery support 8 hours minimum Operating time;

Sound;

Video Camera;

Video Capture Stills & motion;

Serial port support;

Serial USB support;

Send Receive Email;

Transmit fully interactive, two-way audio, video and diagnostic information;

Maintain Patient Data Management System Locally & Main Server;

Wireless cellular Pots;

Support normal Pots Tip & ring, ISDN, ADSL, Cable modem;

Wireless cellular Communications Pots; and

Network Communications.

A general-purpose, low-cost Pocket Device of the present invention provides comprehensive physiological data collection, with extensive data object oriented programmability and configurable for a variety of medical as well as other analog data collection applications. A general-purpose data routing and encapsulation architecture of the present invention supports input tagging and standardized routing through modem packet switch networks, including the Internet; from one of multiple points of origin or patients, to one or multiple points of data analysis for physician review. Real-time data collection, routing, and viewing (or slower than real-time processes when communications infrastructure is slower than the data collection rate). Routing and viewing stations allow for the insertion of automated analysis routines to aid in data encoding, analysis, viewing, and diagnosis.

The Pocket Device of the present invention utilizes communications to transmit fully interactive, two-way audio, video and diagnostic information. The global medical record system of the present invention integrates medical peripherals, a computer and a variety of cameras. A high-resolution camera provides diagnostic quality images to the consulting provider. The camera's zoom, focus and iris control features allow detailed examinations. With the aid of custom and standard adaptors, a micro camera can be connected to an otoscope (ear), an ophthalmoscope (eye) and a microscope. A patient's heart and lung sounds can be transmitted to the consulting provider with the use of an electronic stethoscope. Additional external video cables allow live video from other equipment, such as an ultrasound machine or other image-generating diagnostic devices, to be transmitted over the system. The computer attached to the system has the capability to capture and transmit still images from any of the system's video sources. In addition, the Patient Data Management System provides an electronic complete medical record of the telemedicine consult.

Moreover, the pocket device Global Medical Record system of the present invention provides clinical services and is designed for use by all types of health care providers. The system supports both initial and follow up consultations, established specialty clinics, and emergency consultations. Just as standard referral patterns are typically regional, telemedicine remote sites typically seek consultative care at the nearest telemedicine hub site. Medical specialties using telemedicine most are pediatrics, pulmonary, psychiatry, infectious diseases, and neurology. The ancillary consultations most frequently requested are speech therapy, pediatric nutrition, physical therapy, and occupational therapy. Because of teleconsultation, the number of patients who are able to remain in their local communities without travel for the required specialty access averages more than 93 percent.

FIG. 35 shows a global medical records system 2000. In the global medical records system 2000 shown in FIG. 35, patient data is captured using a computer 2002 at a patient's home. The patient data captured includes photographs, vitals, demographics, and e-mail. The captured patient data is then transmitted by the computer 2002 via e-mail over the Internet 2012 to a repository 2004. The repository 2004 includes a local area network 2006 coupled to a workstation 2008, a patient database 2009, and a mail server 2010. The repository 2004 is operated using a MEDVIZER POSTMASTER, which monitors a post office, receives mail, auto files the mail to a patient database, and sends a notification. Also using the global medical records system 2000, patient records can be viewed at a doctor's home/office through the internet 2012 using MEDVIZER.COM.

FIG. 36 shows a pocket device complete home monitoring system 2100 of the present invention. As shown in FIG. 36, a communication network 2102 interfaces to a hospital 2104 using MEDVIZER POSTMASTER, a WEB server, and a database server; to a Doctor's Home 2106 using MEDVIZER and a WEB thin client; to a hospital 2108 using a MEDVIZER system; to a doctor's office 2110 using a MEDVIZER system; and to a personal digital assistant (PDA) 2112 using a patient monitoring system.

FIG. 37A and FIG. 37B shows a pocket device home monitoring system 2200 of the present invention. As shown in FIG. 37A, the pocket device home monitoring system 2200 includes a pocket device 2112 executing telemedicine application software and interfacing to a communication network 2102, medical devices 1-$n$ 2202, a camera 2204, a network 2206, and a modem 2208. The communication network 2102 also interfaces via e-mail 2210 to a hospital MEDVIZER PostMaster Application software.

As shown in FIG. 37B, the pocket device complete home monitoring system 2200 through the communication network 2102 interfaces to the hospital system 2210 including the MEDVIZER PostMaster, a web server, and a database server. The hospital system 2210 includes the PostMaster 2212 which receives patient data mail, de-encapsulates the data, normalizes the patient data base, and auto files the patient monitoring objects.

Figure 38:
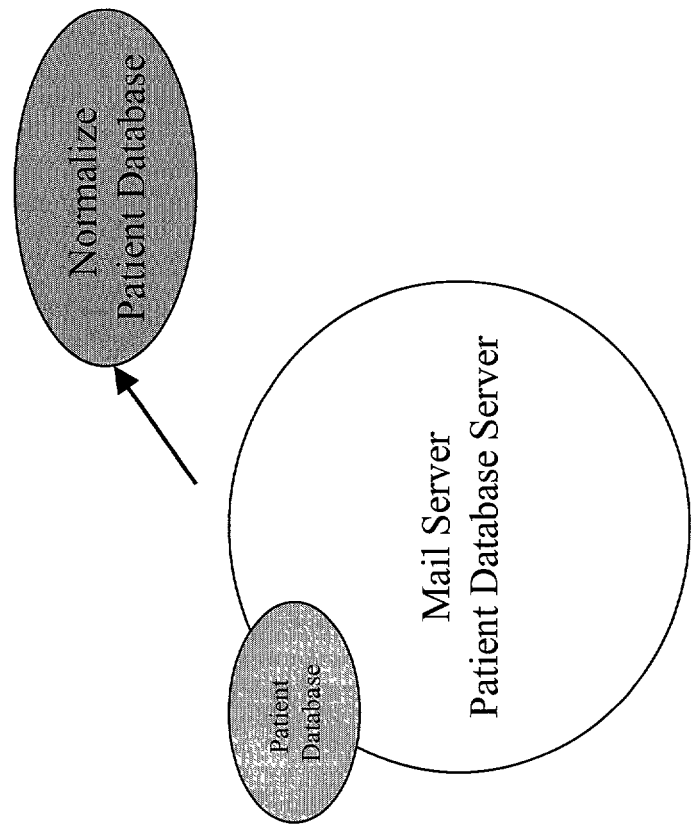
FIG. 38 shows a PostMaster.

FIG. 38 shows an overview of the PostMaster 2212. The MedVizer PostMaster 2212 presents a new approach for the seamless integration of information in a healthcare enterprise, on an intranet or across public and private internets. Patient episode data is captured, compressed, encrypted, and encapsulated into a single secure file and emailed to the mail server where PostMaster processes incoming mail. Complete medical records can be shared in a secure environment regardless of the source of information origin. Information can be pulled from or pushed to Hospital Information Systems (HIS), Picture Archive and Communication Systems (PACS) or Laboratory Information Systems (LIS) using standard HL7 and DICOM 3.0 protocols. Electronic Medical Records can also be shared external to the institution via encrypted SMTP or POP mail messages. A state-of-the-art alert messages center has also been incorporated into the MedVizer PostMaster to alert clinicians when medical information is ready for review.

Key features of the PostMaster 2212 include:
Point to point information transfer system with telephone directory management support;
POP/SMTP secure medical record information distribution facility;
Microsoft Mail Exchange portal for information management and distribution;
Incoming mail is uncompressed and de-encapsulated; and
Automated electronic medical record filing system.

Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An apparatus, comprising:
a server computer configured to execute a medical records system and to:
interface with client computing devices over a data network,
store a master control file to control interoperability of the medical records system on the server with disparate operating systems of the one or more client computing devices by specifying data access and mapping information between a database of text and medical image data of a medical record of the medical records system and the disparate operating systems of the one or more client computing devices over the data network, based upon respective function engines and application program interfaces for the disparate operating systems of the one or more client computing devices, and
serve over the data network multi-form management, device capture management and folder management services of the medical records system for the disparate operation systems of the one or more client computing devices by populating and retrieving information to and from the database of text and medical image data of the medical record responsive to any one of the disparate operating systems of the one or more client computing devices, based upon the specified data access and mapping information of the master control file according to the respective function engines and application program interfaces for the disparate operating systems of the one or more client computing devices.

2. The apparatus as in claim 1, wherein at least a portion of the medical records system is executed by a hand-held device as a client computing device.

3. The apparatus as in claim 1, wherein the master control file controls path and name of folder images, path to and name of the database, database field names, attributes, and locations on the folder image.

4. The apparatus as in claim 3, wherein each field name is retained and utilized by the medical records system when information is populated and retrieved.

5. The apparatus as in claim 3, wherein a pointer to and the name of the database indicates the database which the medical records system will populate and retrieve information from.

6. The apparatus as in claim 3, wherein a pointer to and name of graphic images indicates images that display when the medical records system is executed.

7. The apparatus as in claim 1, wherein the medical record is a patient medical record.

8. The apparatus as in claim 2, wherein the medical records system storing patient medical records enables health care providers to remotely obtain and review complete patient medical records.

9. The apparatus as in claim 2, wherein the medical records system storing patient medical records enables health care providers to view health indicators remotely.

10. The apparatus as in claim 7, wherein the server computer captures, compresses, encrypts, and encapsulates patient episode data for the medical record into a secure file.

11. The apparatus as in claim 10, wherein the server computer transmits the secure file to a repository mail server, which de-encapsulates and uncompresses the secure file and stores the de-encapsulated, uncompressed secure file into a patient medical record.

12. The apparatus as in claim 11, wherein a message is transmitted to an assigned physician notifying the assigned physician of receipt of the patient episode data.

13. A method of interfacing one or more client computing devices with a server computer that executes a medical records system over a data network, comprising:
storing, by the server computer a master control file to control interoperability of the medical records system on the server with disparate operating systems of the one or more client computing devices by specifying data access and mapping information between a database of text and medical image data of a medical record of the medical records system and the disparate operating systems of the one or more client computing devices over the data network, based upon respective function engines and application program interfaces for the disparate operating systems of the one or more client computing devices; and
serving, by the server computer, over the data network multi-form management, device capture management and folder management services of the medical records system for the disparate operation systems of the one or more client computing devices by populating and retrieving information to and from the database of text and medical image data of the medical record responsive to any one of the disparate operating systems of the one or more client computing devices, based upon the specified data access and mapping information of the master control file according to the respective function engines and application program interfaces for the disparate operating systems of the one or more client computing devices.

14. The method as in claim 13, wherein at least a portion of the medical records system is executed by a hand-held device as a client computing device.

15. The method as in claim 13, wherein the master control file controls path and name of folder images, path to and name of the database, database field names, attributes, and locations on the folder image.

16. The method as in claim 15, further comprising retaining and utilizing each field name by the medical records system when information is populated and retrieved.

17. The method as in claim 16, further comprising indicating, by a pointer to and the name of the database, the database which the medical records system will populate and retrieve information from.

18. The method as in claim 16, further comprising indicating, by a pointer to and name of graphic images, images that display when the medical records system is executed.

19. The method as in claim 14, further comprising storing patient medical records in the medical records system.

20. The method as in claim 14, further comprising storing patient medical records to enable health care providers to remotely obtain and review complete patient medical records.

21. The method as in claim 13, further comprising storing patient medical records to enable health care providers to view health indicators remotely.

22. The method as in claim 13, further comprising capturing, compressing, encrypting, and encapsulating, by the server computer, patient episode data for the medical record into a secure file.

23. The method as in claim 22, further comprising:
transmitting, by the server computer, the secure file to a repository mail server,
de-encapsulating and uncompressing, by the repository mail server, the secure file, and
storing, by the repository mail server, the de-encapsulated, uncompressed secure file into a patient medical record.

24. The method as in claim 23, further comprising notifying, by the server computer, an assigned physician of receipt of the patient episode data.

25. A non-transitory computer-readable medium storing a program executed by a server computer with a medical records system to interface with one or more client computing devices by executing functions comprising:
storing by the server computer a master control file to control interoperability of the medical records system on the server with disparate operating systems of the one or more client computing devices by specifying data access and mapping information between a database of text and medical image data of a medical record of the medical records system and the disparate operating systems of the one or more client computing devices over the data network, based upon respective function engines and application program interfaces of the disparate operating systems for the one or more client computing devices; and
serving by the server computer over the data network multi-form management, device capture management and folder management services of the medical records system for the disparate operation systems of the one or more client computing devices by populating and retrieving information to and from the database of text and medical image data of the medical record responsive to any one of the disparate operating systems of the one or more client computing devices, based upon the specified data access and mapping information of the master control file according to the respective function engines and application program interfaces for the disparate operating systems of the one or more client computing devices.

26. The computer-readable medium as in claim 25, wherein at least a portion of the medical records system is executed by a hand-held device as a client computing device.

27. The computer-readable medium as in 25, wherein the master control file controls path and name of folder images, path to and name of the database, database field names, attributes, and locations on the folder image.

28. The computer-readable medium as in claim 27, further comprising retaining and utilizing each field name by the medical records system when information is populated and retrieved.

29. The computer-readable medium as in claim 27, further comprising indicating, by a pointer to and the name of the database, the database which the medical records system will populate and retrieve information from.

30. The computer-readable medium as in claim 27, further comprising indicating, by a pointer to and name of graphic images, images that display when the medical records system is executed.

31. The computer-readable medium as in claim 26, further comprising storing patient medical records in the medical records system.

32. The computer-readable medium as in claim 26, further comprising storing patient medical records to enable health care providers to remotely obtain and review complete patient medical records.

33. The computer-readable medium as in claim 25, further comprising storing patient medical records to enable health care providers to view health indicators remotely.

34. The computer-readable medium as in claim 25, further comprising capturing, compressing, encrypting, and encapsulating, by the server computer, patient episode data for the medical record into a secure file.

35. The computer-readable medium as in claim 34, further comprising:
transmitting, by the server computer, the secure file to a repository mail server,
de-encapsulating and uncompressing, by the repository mail server, the secure file, and
storing, by the repository mail server, the de-encapsulated, uncompressed secure file into a patient medical record.

36. The computer-readable medium as in claim 35, further comprising notifying the assigned physician of receipt of the patient episode data.

* * * * *

UNITED STATES PATENT AND TRADEMARK OFFICE
CERTIFICATE OF CORRECTION

| | | |
|---|---|---|
| PATENT NO. | : 8,751,248 B2 | Page 1 of 1 |
| APPLICATION NO. | : 09/853703 | |
| DATED | : June 10, 2014 | |
| INVENTOR(S) | : John Muraca | |

It is certified that error appears in the above-identified patent and that said Letters Patent is hereby corrected as shown below:

In the Claims

Column 30, Line 14, in Claim 27, delete "in 25," and insert -- in claim 25, --, therefor.

Signed and Sealed this
Twenty-third Day of September, 2014

Michelle K. Lee
*Deputy Director of the United States Patent and Trademark Office*